United States Patent

Takemura et al.

[11] Patent Number: 5,308,829
[45] Date of Patent: May 3, 1994

[54] BENBZOFURAN DERIVATIVES AND THEIR USE AS HERBICIDES

[75] Inventors: Susumu Takemura, Takarazuka; Masayuki Enomoto, Nishinomiya; Toru Uekawa, Takarazuka; Masaharu Sakaki, Toyonaka, all of Japan; Ryo Sato, Durham; Eiki Nagano, Raleigh, both of N.C.

[73] Assignee: Sumitomo Chemical Company, Limited, Osaka, Japan

[21] Appl. No.: 38,564

[22] Filed: Mar. 18, 1993

[30] Foreign Application Priority Data

Mar. 18, 1992 [JP] Japan ................... 4-062251

[51] Int. Cl.$^5$ ................ A01N 43/54; C07D 405/10
[52] U.S. Cl. ...................... 504/243; 549/310; 549/467; 564/442; 564/443
[58] Field of Search .................. 544/310; 504/243

[56] References Cited

U.S. PATENT DOCUMENTS

| | | | |
|---|---|---|---|
| 4,859,229 | 8/1989 | Wenger et al. | 504/243 |
| 4,881,967 | 11/1989 | Semple | 504/221 |
| 5,084,084 | 1/1992 | Satow et al. | 504/225 |
| 5,116,404 | 5/1992 | Ishii et al. | 504/193 |
| 5,169,431 | 12/1992 | Enomoto et al. | 544/310 |

FOREIGN PATENT DOCUMENTS

| | | |
|---|---|---|
| 0255047 | 2/1988 | European Pat. Off. |
| 0408382 | 1/1991 | European Pat. Off. |
| 0420194 | 4/1991 | European Pat. Off. |
| 0438209 | 7/1991 | European Pat. Off. |
| 0476697 | 3/1992 | European Pat. Off. |
| 0517181 | 12/1992 | European Pat. Off. |

*Primary Examiner*—Emily Bernhardt
*Attorney, Agent, or Firm*—Birch, Stewart, Kolasch & Birch

[57] ABSTRACT

There are disclosed novel benzofuran derivatives of the formula:

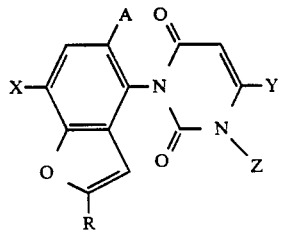

Also disclosed are a herbicidal composition containing the above benzofuran derivative as an active ingredient and a method for exterminating undesired 7eeds by the application of a herbicidally effective amount of the above benzofuran derivative to an area where the undesired 7eeds grow or 7ill grow.

14 Claims, No Drawings

BENBZOFURAN DERIVATIVES AND THEIR USE AS HERBICIDES

FIELD OF THE INVENTION

The present invention relates to novel benzofuran derivatives and herbicidal compositions containing them as active ingredients.

BACKGROUND OF THE INVENTION

It is well known in the art that certain kinds of substituted benzofuran can be used as active ingredients for herbicides (see, e.g., U.S. Pat. /. 4,881,967).

These compounds, however, have insufficient herbicidal activity and poor selectivity between crop plants and 7eeds, and it cannot always be said that they are satisfactory for active ingredients for herbicides.

SUMMARY OF THE INVENTION

Under these circumstances, the present inventors have intensively studied various compounds. As the result, they have found that particular kinds of benzofuran derivatives have excellent herbicidal activity and excellent selectivity between crop plants and weeds, thereby completing the present invention.

That is, the present invention provides novel benzofuran derivatives of the general formula:

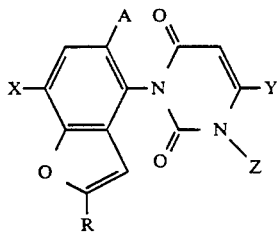

(I)

7herein A is hydrogen, fluorine or chlorine; X is hydrogen, fluorine, chlorine or bromine; Y is methyl opti/-nally substituted with halogen; Z is methyl or amino; R is halo($C_1$–$C_5$)alkyl, ($C_1$–$C_5$)alkylthio($C_1$–$C_5$)alkyl, amino($C_1$–$C_5$)alkyl, ($C_1$–$C_5$)alkylamino($C_1$–$C_5$)alkyl, ($C_1$–$C_5$)acylamino($C_1$–$C_5$)alkyl, ($C_1$–$C_5$)alkylsulfonylamino($C_1$–$C_5$)alkyl, $C_1$–$C_5$ acyl, hydroxy($C_1$–$C_5$)alkyl, ($C_1$–$C_5$)alkoxy($C_1$–$C_5$)alkyl, ($C_1$–$C_5$)alkoxy($C_1$–$C_5$)alkoxy($C_1$–$C_5$)alkyl, ($C_1$–$C_5$)acyloxy($C_1$–$C_5$)alkyl, hydroxyimino($C_1$–$C_5$)alkyl, ($C_1$–$C_5$)alkoxyimino($C_1$–$C_5$)alkyl, cyano, hydrazono($C_1$–$C_5$)alkyl, ($C_1$–$C_5$)alkylhydrazono($C_1$–$C_5$)alkyl, phenylhydrazono($C_1$–$C_5$)alkyl (7herein the phenyl is optionally substituted 7ith $C_1$–$C_5$ alkyl, $C_1$–$C_5$ alkoxy, halo($C_1$–$C_5$)alkyl, halo($C_1$–$C_5$)alkoxy, halogen, nitro, cyano or $C_1$–$C_5$ alkylthio), carboxy, $C_1$–$C_5$ alkoxycarbonyl, aminocarbonyl, $C_1$–$C_5$ alkylaminocarbonyl or phenylaminocarbonyl (7herein the phenyl is optionally substituted 7ith $C_1$–$C_5$ alkyl, $C_1$–$C_5$ alkoxy, halo($C_1$–$C_5$)alkyl, halo($C_1$–$C_5$)alkoxy, halogen, nitro, cyano or $C_1$–$C_5$ alkylthio).

As used herein, the term acyl includes formyl, $C_1$–$C_4$ alkylcarbonyl and halo($C_1$–$C_4$)alkylcarbonyl.

The present invention also provides a herbicidal composition containing a herbicidally effective amount of the compound (I) as an active ingredient and a method of exterminating undesired weeds by applying a herbicidally effective amount of the compound (I) to an area 7here the undesired 7eeds grow or will grow.

DETAILED DESCRIPTION OF THE INVENTION

Among the compounds (I) of the present invention, preferred are those wherein A is fluorine or chlorine, X is fluorine or chlorine, Y is trifluoromethyl or chlorodifluoromethyl, Z is methyl and R is halo($C_1$–$C_5$)alkyl, $C_1$–$C_5$ acyl, hydroxy($C_1$–$C_5$)alkyl, ($C_1$–$C_5$)alkoxy($C_1$–$C_5$)alkyl, ($C_1$–$C_5$)alkoxy($C_1$–$C_5$)alkoxy($C_1$–$C_5$)alkyl, ($C_1$–$C_5$)acyloxy($C_1$–$C_5$)alkyl, hydroxyimino($C_1$–$C_5$)alkyl, ($C_1$–$C_5$)alkoxyimino($C_1$–$C_5$)alkyl, cyano, ($C_1$–$C_5$)alkylhydrazono($C_1$–$C_5$)alkyl, carboxy, $C_1$–$C_5$ alkoxycarbonyl or amino carbonyl. Among these preferred compounds, more preferred are those wherein A is fluorine and Y is trifluoromethyl, or those 7here R is hydroxy($C_1$–$C_5$)alkyl, ($C_1$–$C_5$)alkoxy($C_1$–$C_5$)alkyl, ($C_1$–$C_5$)acyloxy($C_1$–$C_5$)alkyl, carboxy or $C_1$–$C_5$ alkoxycarbonyl. Still more preferred are those having a combination of A, Y and R for the more preferred compounds as described above.

Specific examples of the compounds (I) of the present invention 7hich are particularly preferred are 1-(2-carboxy-7-chloro-5-fluorobenzo[b]furan-4-yl)-3-methyl-4-trifluoromethyl-1,2,3,6-tetrahydropyrimidin-2,6-dione, 1-(7-chloro-5-fluoro-2-methoxycarbonylbenzo[b]furan-4-yl)-3-methyl-4-trifluoromethyl-1,2,3,6-tetrahydropyrimidin-2,6-dione, 1-(5,7-difluoro-2-hydroxymethylbenzo[b]furan-4-yl)-3-methyl-4-trifluoromethyl-1,2,3,6-tetrahydropyrimidin-2,6-dione and 1-(2-acetoxymethyl-5,7-difluorobenzo[b]furan-4-yl)-3-methyl-4-trifluoromethyl-1,2,3,6-tetrahydropyrimidin-2,6-dione.

The following 7ill describe various production processes for the compounds (I) of the present invention.

Production Process (a)

The particular compound (I) 7herein R is halo($C_1$–$C_5$)alkyl can be produced, for example, as a mixture of a compound of the general formula:

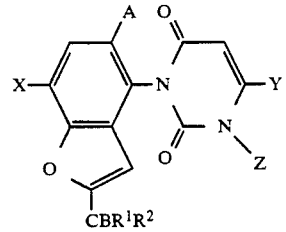

(I-1)

7herein A is hydrogen, fluorine or chlorine; B is halogen; X is hydrogen, fluorine, chlorine or bromine; Y is methyl optionally substituted with halogen; Z is methyl or amino; and $R^1$ and $R^2$ are the same or different and are hydrogen or $C_1$–$C_4$ alkyl, 7ith the proviso that the total carbon atom number of $R^1$ and $R^2$ is 4 or less; a compound of the general formula:

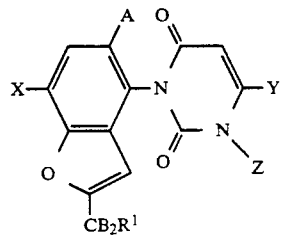

(I-2)

wherein A, B, X, Y, Z and $R^1$ are each as defined above; and a compound of the general formula:

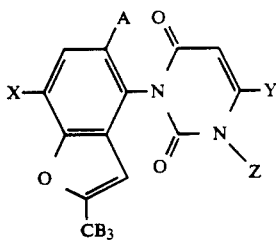

(I-3)

wherein A, B, X, Y and Z are each as defined above, by reacting a compound of the formula:

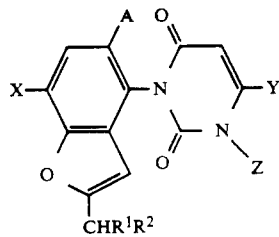

(II)

wherein A, X, Y, Z, $R^1$ and $R^2$ are each as defined above, with a halogenating agent. In this case, however, the compound (I-2) can be obtained only when $R^2$ of the compound (II) is hydrogen, and the compound (I-3) can be obtained only when $R^1$ and $R^2$ of the compound (II) are both hydrogen. The desired compound can be obtained by isolating and purifying these compounds obtained as a mixture.

The reaction is usually carried out in an inert solvent with or without a catalyst at a temperature of about 0° to 150° C., preferably about 20° to 80° C., for a period of about 0.5 to 24 hours. The halogenating agent and the catalyst are used in amounts of 1 to 10 equivalents and of 0.01 to 0.5 equivalents, respectively, to one equivalent of the compound (II).

Examples of the halogenating agent are halogens such as bromine and chlorine; N-halosuccinimides such as -bromosuccinimide; and pyridinium salts such as pyridinium perbromide.

Examples of the inert solvent are halogenated hydrocarbons such as chloroform and carbon tetrachloride; carboxylic acids such as formic acid and acetic acid; amides such as N,N-dimethylformamide; and sulfur compounds such as dimethylsulfoxide and sulfolane. Examples of the catalyst are benzoyl peroxide, α,α'-azobisisobutyronitrile and mixtures thereof.

After completion of the reaction, the reaction mixture is subjected to ordinary post-treatment. For instance, the reaction mixture is filtered, if necessary, to remove undissolved matter contained therein and poured into water, and the precipitated crystals are collected by filtration or the resultant mixture is extracted with an organic solvent, followed by concentration. If desired, any conventional purification procedure such as chromatography or recrystallization may be applied to the resulting product, thus obtaining the desired compound.

Production Process (b)

The particular compound (I) wherein R is ($C_1$-$C_5$)alkylthio($C_1$-$C_5$)alkyl can be produced by reacting the compound (I-1), which is obtained by the above production process (a), with a compound of the general formula:

$$R^3SH \quad (III)$$

wherein $R^3$ is $C_1$-$C_5$ alkyl.

The reaction is usually carried out in an inert solvent in the presence of a base at a temperature of about 0° to 100° C., preferably about 20° to 60° C., for a period of about 0.5 to 24 hours. The compound (III) and the base are used in amounts of 1 to 5 equivalents and of 1 to 10 equivalents, respectively, to one equivalent of the compound (I-1).

Examples of the inert solvent are ethers such as tetrahydrofuran and dioxane; amides such as N,N-dimethylformamide; and sulfur compounds such as dimethylsulfoxide and sulfolane. Examples of the base are metal hydroxides such as sodium hydroxide and potassium hydroxide; and metal alkoxides such as sodium methoxide.

After completion of the reaction, the reaction mixture is subjected to ordinary post-treatment. For instance, the reaction mixture is poured into water, and the precipitated crystals are collected by filtration or the resultant mixture is extracted with an organic solvent, followed by concentration. If desired, any conventional purification procedure such as chromatography or recrystallization may be applied to the resulting product, thus obtaining the desired compound.

Production Process (c)

The particular compound (I) wherein R is amino($C_1$-$C_5$)alkyl, ($C_1$-$C_5$)alkylamino($C_1$-$C_5$)alkyl, ($C_1$-$C_5$)acylamino($C_1$-$C_5$)alkyl or ($C_1$-$C_5$)alkylsulfonylamino($C_1$-$C_5$)alkyl can be produced by reacting the compound (I-1), which is obtained by the above production process (a), with a compound of the general formula:

$$R^4R^5NH \quad (IV)$$

wherein $R^4$ and $R^5$ are the same or different and are hydrogen, $C_1$-$C_5$ alkyl, $C_1$-$C_5$ acyl or $C_1$-$C_5$ alkylsulfonyl, with the proviso that the total carbon atom number of $R^4$ and $R^5$ is 5 or less.

The reaction is usually carried out in an inert solvent in the presence of a base at a temperature of about 0° to 100° C., preferably about 20° to 80° C., for a period of about 0.5 to 24 hours. The compound (IV) and the base are used in amounts of 1 to 5 equivalents and of 1 to 10 equivalents, respectively, to one equivalent of the compound (I-1).

Examples of the inert solvent are ethers such as tetrahydrofuran and dioxane; amides such as N,N-dimethylformamide; sulfur compounds such as dimethylsulfoxide and sulfolane; and aromatic hydrocarbons such as benzene and toluene. Examples of the base are metal hydrides such as sodium hydride and potassium hydride.

After completion of the reaction, the reaction mixture is subjected to ordinary post-treatment. For instance, the reaction mixture is poured into water, and the precipitated crystals are collected by filtration or the resultant mixture is extracted with an organic solvent, followed by concentration. If desired, any conventional purification procedure such as chromatography or recrystallization may be applied to the resulting product, thus obtaining the desired compound.

Production Process (d)

The particular compound (I) wherein R is $C_1$-$C_5$ acyl can be produced by hydrolyzing the compound (I-2) which is obtained by the above production process (a).

The reaction is usually carried out with or without an inert solvent in the presence of an acid at a temperature of about 0° to 150° C., preferably about 20° to 80° C., for a period of about 0.5 to 12 hours. The acid is used in an amount of 0.01 to 100 equivalents to one equivalent of the compound (I-2).

Examples of the inert solvent are ethers such as tetrahydrofuran and dioxane; alcohols such as methanol and ethanol; carboxylic acids such as formic acid and acetic acid; mineral acids such as hydrochloric acid and sulfuric acid; water and mixtures thereof. Examples of the acid are mineral acids such as hydrochloric acid and sulfuric acid; and sulfonic acids such as p-toluenesulfonic acid and methanesulfonic acid.

After completion of the reaction, the reaction mixture is subjected to ordinary post-treatment. F/r instance, the reaction mixture is poured into water, and the precipitated crystals are collected by filtration or the resultant mixture is extracted with an organic solvent, followed by concentration. If desired, any conventional purification procedure such as chromatography or recrystallization may be applied to the resulting product, thus obtaining the desired compound.

Production Process (e)

The particular compound (I) wherein R is hydroxy($C_1$-$C_5$)alkyl can be produced by reducing the particular compound (I) wherein R is $C_1$-$C_5$ acyl, which is obtained by the above production process (d), with a reducing agent.

The reaction is usually carried out in an inert solvent at a temperature of about −80° to 40° C., preferably about 0° to 20° C., for a period of about 0.5 to 12 hours. The reducing agent is used in an amount of 0.25 to 2 mols to one mol of the particular compound (I) wherein R is $C_1$-$C_5$ acyl.

Examples of the reducing agent are sodium borohydride, lithium aluminum hydride and diisobutylaluminum hydride. Examples of the solvent are aliphatic hydrocarbons such as hexane and heptane; and ethers such as diethyl ether and tetrahydrofuran.

After completion of the reaction, the reaction mixture is subjected to ordinary post-treatment. F/r instance, the reaction mixture is poured into water, and the precipitated crystals are collected by filtration or the resultant mixture is extracted with an organic solvent, followed by concentration. If desired, any conventional purification procedure such as chromatography or recrystallization may be applied to the resulting product, thus obtaining the desired compound.

Production Process (f)

The particular compound (I) wherein R is ($C_1$-$C_5$)acyloxy($C_1$-$C_5$)alkyl can be produced by reacting the particular compound (I) wherein R is hydroxy($C_1$-$C_5$)alkyl, which is obtained by the above production process (e), with a compound of the general formula:

$$R^6G \quad (V)$$

wherein $R^6$ is $C_1$-$C_5$ acyl and G is chlorine or bromine; or with a compound of the formula:

$$(R^6)_2O \quad (VI)$$

wherein $R^6$ is as defined above.

The reaction is usually carried out with or without an inert solvent in the presence of a base at a temperature of about 0° to 40° C., preferably about 5° to 30° C., for a period of about 0.5 to 24 hours. The compound (V) or (I) and the base are used in amounts of 1 to 5 equivalents and of 1 to 100 equivalents, respectively, to one equivalent of the particular compound (I) wherein R is hydroxy($C_1$-$C_5$)alkyl.

Examples of the inert solvent are ethers such as diethyl ether and tetrahydrofuran; and tertiary amines such as triethylamine and pyridine. Examples of the base are tertiary amines such as pyridine, 4-dimethylaminopyridine and triethylamine; and metal hydrides such as sodium hydride.

After completion of the reaction, the reaction mixture is subjected to ordinary post-treatment. F/r instance, the reaction mixture is poured into water, and the precipitated crystals are collected by filtration or the resultant mixture is extracted with an organic solvent, followed by concentration. If desired, any conventional purification procedure such as chromatography or recrystallization may be applied to the resulting product, thus obtaining the desired compound.

Production Process (g)

The particular compound (I) wherein R is hydroxyimino($C_1$-$C_5$)alkyl or ($C_1$-$C_5$)alkoxyamino($C_1$-$C_5$)alkyl can be produced by reacting the particular compound (I) wherein R is $C_1$-$C_5$ acyl, which is obtained by the above production process (d), with a hydrochloric acid salt or sulfuric acid salt of a compound of the general formula:

$$NH_2OR^7 \quad (VII)$$

wherein $R^7$ is hydrogen or $C_1$-$C_5$ alkyl.

The reaction is usually carried out in an inert solvent in the presence of a base at a temperature of about 0° to 100° C., preferably about 20° to 60° C., for a period of about 0.5 to 12 hours. The hydrochloric acid salt or sulfuric acid salt of the compound (VII) and the base are used in amounts of 1 to 5 equivalents and of 1 to 10 equivalents, respectively, to one equivalent of the particular compound (I) wherein R is $C_1$-$C_5$ acyl.

Examples of the inert solvent are ethers such as tetrahydrofuran and dioxane; alcohols such as methanol and ethanol; amides such as N,N-diemthylformamide; water and mixtures thereof. Examples of the base are metal carbonates such as potassium carbonate and sodium carbonate; metal acetates such as sodium acetate and potassium acetate; and amines such as triethylamine and dimethylamine.

A&ter completion of the reaction, the reaction mixture is subjected to ordinary post-treatment. F/r instance, the reaction mixture is poured into water, and the precipitated crystals are collected by filtration or the resultant mixture is extracted with an organic solvent, followed by concentration. If desired, any conventional purification procedure such as chromatography or recrystallization may be applied to the resulting product, thus obtaining the desired compound.

Production Process (h)

The particular compound (I) wherein R is cyano can be produced by dehydrating the particular compound (I) wherein R is hydroxyiminomethyl, which is obtained by the above production process (g).

The reaction is usually carried out in an inert solvent at a temperature of about 60° to 200° C., preferably about 80° to 150° C., for a period of about 0.5 to 24 hours.

Examples of the inert solvent are alcohols such as ethanol and propanol; amides such as N,N-dimethylformamide; sulfur compounds such as dimethylsulfoxide and sulfolane; and aromatic hydrocarbons such as toluene and xylene.

After completion of the reaction, the reaction mixture is subjected to ordinary post-treatment. For instance, the reaction mixture is poured into water, and the precipitated crystals are collected by filtration or the resultant mixture is extracted with an organic solvent, followed by concentration. If desired, any conventional purification procedure such as chromatography or recrystallization may be applied to the resulting product, thus obtaining the desired compound.

Production Process (i)

The particular compound (I) wherein R is hydrazono($C_1$-$C_5$)alkyl, ($C_1$-$C_5$)alkylhydrazono($C_1$-$C_5$)alkyl or phenylhydrazono($C_1$-$C_5$)alkyl (wherein the phenyl is optionally substituted with $C_1$-$C_5$ alkyl, $C_1$-$C_5$ alkoxy, halo($C_1$-$C_5$)alkyl, halo($C_1$-$C_5$)alkoxy, halogen, nitro, cyano or $C_1$-$C_5$ alkylthio) can be produced by reacting the particular compound (I) wherein R is $C_1$-$C_5$ acyl, which is obtained by the above production process (d), with a compound of the general formula:

$$NH_2NR^8R^9 \qquad (VIII)$$

wherein $R^8$ and $R^9$ are the same or different and are hydrogen, $C_1$-$C_5$ alkyl or phenyl (wherein the phenyl is optionally substituted with $C_1$-$C_5$ alkyl, $C_1$-$C_5$ alkoxy, halo($C_1$-$C_5$)alkyl, halo($C_1$-$C_5$)alkoxy, halogen, nitro, cyano or $C_1$-$C_5$ alkylthio).

The reaction is usually carried out in an inert solvent at a temperature of about 0° to 150° C., preferably about 20° to 80° C., for a period of about 0.5 to 24 hours. The compound (VIII) is used in an amount of 1 to 10 equivalents to one equivalent of the particular compound (I) wherein R is $C_1$-$C_5$ acyl.

Examples of the inert solvent are ethers such as tetrahydrofuran and dioxane; alcohols such as methanol and ethanol; and aromatic hydrocarbons such as benzene and toluene; and water.

After completion of the reaction, the reaction mixture is subjected to ordinary post-treatment. For instance, the reaction mixture is poured into water, and the precipitated crystals are collected by filtration or the resultant mixture is extracted with an organic solvent, followed by concentration. If desired, any conventional purification procedure such as chromatography or recrystallization may be applied to the resulting product, thus obtaining the desired compound.

Production Process (j)

The particular compound (I) wherein R is ($C_1$-$C_5$)alkoxy($C_1$-$C_5$)alkyl or ($C_1$-$C_5$)alkoxy($C_1$-$C_5$)alkoxy($C_1$-$C_5$)alkyl can be produced by reacting the particular compound (I) wherein R is hydroxy($C_1$-$C_5$)alkyl, which is obtained by the above production process (e), with a compound of the general formula:

$$R^{10}J \qquad (IX)$$

wherein $R^{10}$ is $C_1$-$C_5$ alkyl or ($C_1$-$C_5$)alkoxy($C_1$-$C_5$)alkyl; and J is halogen, methanesulfonyloxy or p-toluenesulfonyloxy.

The reaction is usually carried out in an inert solvent in the presence of a base at a temperature of about 0° to 150° C., preferably about 5° to 50° C., for a period of about 0.5 to 24 hours. The compound (IX) and the base are used in amounts of 1 to 10 equivalents and of 1 to 5 equivalents, respectively, to one equivalent of the particular compound (I) wherein R is hydroxy($C_1$-$C_5$)alkyl.

Examples of the inert solvent are ethers such as diethylether, tetrahydrofuran and dioxane; aromatic hydrocarbons such as benzene and toluene; and amides such as N,N-dimethylformamide. Examples of the base are inorganic bases such as potassium carbonate and sodium hydride.

After completion of the reaction, the reaction mixture is subjected to ordinary post-treatment. For instance, the reaction mixture is poured into water, and the precipitated crystals are collected by filtration or the resultant mixture is extracted with an organic solvent, followed by concentration. If desired, any conventional purification procedure such as chromatography or recrystallization may be applied to the resulting product, thus obtaining the desired compound.

Production Process (k)

The particular compound (I) wherein R is carboxy can be produced by hydrolyzing the compound (I-3) which is obtained in the above production process (a).

The reaction is usually carried out with or without an inert solvent in the presence of an acid at a temperature of about 0° to 150° C., preferably about 20° to 80° C., for a period of about 0.5 to 12 hours. The acid is used in an amount of 0.01 to 100 equivalents to one equivalent of the particular compound (I-3).

Examples of the inert solvent are ethers such as tetrahydrofuran and dioxane; alcohols such as methanol and ethanol; carboxylic acids such as formic acid and acetic acid; mineral acids such as hydrochloric acid and sulfuric acid; water and mixtures thereof. Examples of the acid are mineral acids such as hydrochloric acid and sulfuric acid; and sulfonic acids such as p-toluenesulfonic acid and methanesulfonic acid.

After completion of the reaction, the reaction mixture is subjected to ordinary post-treatment. For instance, the reaction mixture is poured into water, and the precipitated crystals are collected by filtration or the resultant mixture is extracted with an organic solvent, followed by concentration. If desired, any conventional purification procedure such as chromatography or recrystallization may be applied to the resulting product, thus obtaining the desired compound.

Production Process (l)

The particular compound (I) wherein R is carboxy can also be produced by oxidizing the particular compound (I) wherein R is formyl, which is obtained by the above production process (d), with an oxidizing agent.

The reaction is usually carried out in an inert solvent at a temperature of about −80° to 100° C., preferably about 0° to 50° C., for a period of about 0.5 to 12 hours. The oxidizing agent is used in an amount of 0.5 to 100 mols to one mol of the particular compound (I) wherein R is formyl.

Examples of the oxidizing agent are manganese compounds such as potassium permanganate; chromium compounds such as chromium trioxide; and oxygen gas. Examples of the inert solvent are ketones such as acetone; carboxylic acid such as acetic acid; halogenated hydrocarbons such as dichloromethane and chloroform; water and mixtures thereof.

After completion of the reaction, the reaction mixture is subjected to ordinary post-treatment. For instance, the reaction mixture is poured into water, and the precipitated crystals are collected by filtration or the resultant mixture is extracted with an organic solvent, followed by concentration. If desired, any conventional purification procedure such as chromatography or recrystallization may be applied to the resulting product, thus obtaining the desired compound.

Production Process (M)

The particular compound (I) wherein R is $C_1$–$C_5$ alkoxycarbonyl can be produced by reacting the particular compound (I) wherein R is carboxy, which is obtained by the above production process (k) or (l), with a compound of the general formula:

$$R^{11}OH \quad (X)$$

wherein $R^{11}$ is $C_1$–$C_5$ alkyl.

The reaction is usually carried out with or without an inert solvent in the presence of an acid at a temperature of about 20° to 200° C., preferably about 60° to 120° C., for a period of about 0.5 to 24 hours. The compound (X) and the acid are used in amounts of 1 to 100 equivalents and of 0.001 to 0.5 equivalents, respectively, to one equivalent of the particular compound (I) wherein R is carboxy.

Examples of the acid are mineral acids such as hydrochloric acid and sulfuric acid; and sulfonic acids such as p-toluenesulfonic acid. Examples of the inert solvent are aromatic hydrocarbons such as benzene and toluene; and ethers such as tetrahydrofuran and dioxane.

After completion of the reaction, the reaction mixture is subjected to ordinary post-treatment. For instance, the reaction mixture is poured into water, and the precipitated crystals are collected by filtration or the resultant mixture is extracted with an organic solvent, followed by concentration. If desired, any conventional purification procedure such as chromatography or recrystallization may be applied to the resulting product, thus obtaining the desired compound.

Production Process (N)

The particular compound (I) wherein R is aminocarbonyl, $C_1$–$C_5$ alkylaminocarbonyl or phenylaminocarbonyl (wherein the phenyl is optionally substituted with $C_1$–$C_5$ alkyl, $C_1$–$C_5$ alkoxy, halo($C_1$–$C_5$)alkyl, halo($C_1$–$C_5$)alkoxy, halogen, nitro, cyano or $C_1$–$C_5$ alkylthio) can be produced by reacting the particular compound (I) wherein R is carboxy, which is obtained by the above production process (k) or (l), with thionyl chloride (the first step), and then reacting it with a compound of the general formula:

$$R^8R^9H \quad (XI)$$

wherein $R^8$ and $R^9$ are each as defined above (the second step).

The reaction in the first step is usually carried out with or without an inert solvent at a temperature of about 0° to 100° C., preferably about 20° to 70° C., for a period of about 0.5 to 12 hours. The thionyl chloride is used in an amount of 1 to 100 equivalents to one equivalent of the particular compound (I) wherein R is carboxy.

Examples of the inert solvent which can be used in the first step are halogenated hydrocarbons such as dichloromethane and chloroform; aromatic hydrocarbons such as benzene and toluene; and ethers such as diethyl ether and tetrahydrofuran.

After completion of the reaction, the solvent and excess thionyl chloride may be distilled off, if necessary, thus obtaining a residue which can be used in the second step without conducting any further treatment.

The reaction in the second step is usually carried out with or without an inert solvent at a temperature of about 0° to 100° C., preferably about 5° to 40° C., for a period of about 0.5 to 12 hours. The compound (XI) is used in an amount of 1 to 100 equivalents to one equivalent of the particular compound (I) wherein R is carboxy, which has been used in the first step.

Examples of the inert solvent which can be used in the second step are halogenated hydrocarbons such as dichloromethane and chloroform; aromatic hydrocarbons such as benzene and toluene; and ethers such as diethyl ether and tetrahydrofuran.

After completion of the reaction, the reaction mixture is subjected to ordinary post-treatment. For instance, the reaction mixture is poured into water, and the precipitated crystals are collected by filtration or the resultant mixture is extracted with an organic solvent, followed by concentration. If desired, any conventional purification procedure such as chromatography or recrystallization may be applied to the resulting product, thus obtaining the desired compound.

Production Process (O)

The particular compound (I) wherein R is 1-hydroxyethyl can be produced by reacting the particular compound (I) wherein R is formyl, which is obtained by the above production process (d), with methylmagnesium bromide in tetrahydrofuran at a temperature of about −80° C. to room temperature for a period of about 1 to 2 hours.

Production Process (P)

The particular compound (I) wherein R is acetyl can be produced by oxidizing the particular compound (I) wherein R is 1-hydroxyethyl, which is obtained by the above production process (e) or (o), with Jones reagent (a mixed solution of chromium trioxide, sulfuric acid and water) at a temperature of about −5° C. to room temperature.

Production Process (Q)

The particular compound (I) wherein R is methoxycarbonyl can be produced by reacting the particular compound (I) wherein R is carboxy, which is obtained by the above production process (k) or (l), with diazomethane in methanol at a temperature of about 0° to 5° C.

Production Process (R)

The particular compound (I) 7herein R is cyano and Z is methyl can be produced by refluxing the particular compound (I) 7herein R is formyl and Z is methyl, which is obtained by the above production process (d), together with hydroxylamine (usually used as stable salts such as hydroxyamine hydrochloride) in N,N-dimethylformamide for a period of about 3 hours.

The compound (II) can be produced through the following reaction scheme according to the method as described in EP-A 476 697.

Reaction Scheme for Production of C/mpound (II)

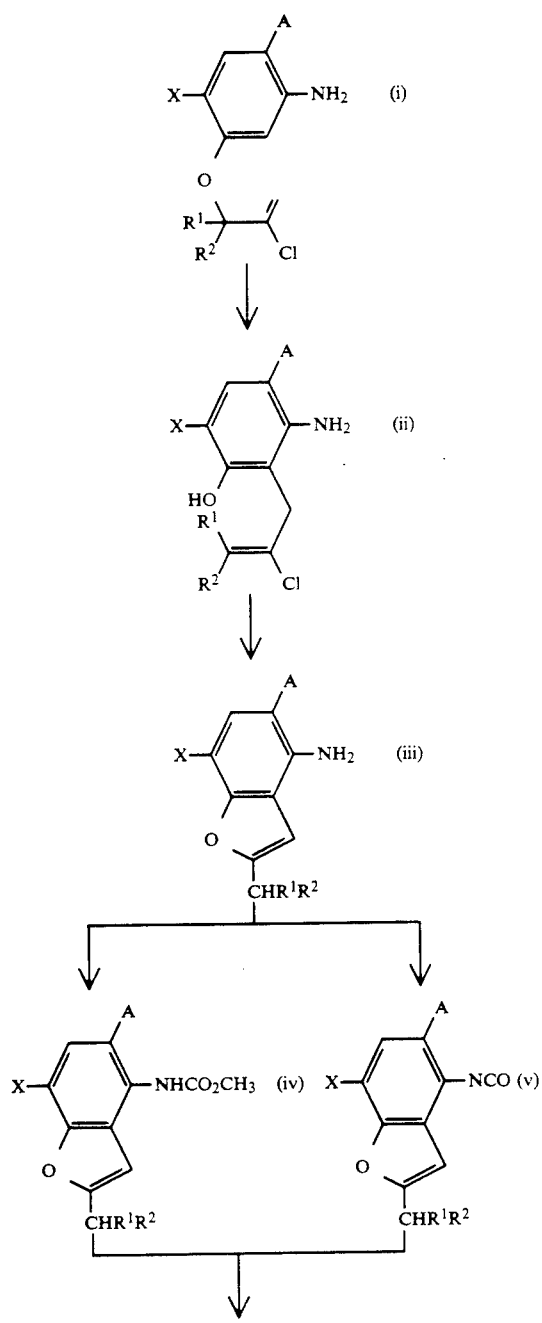

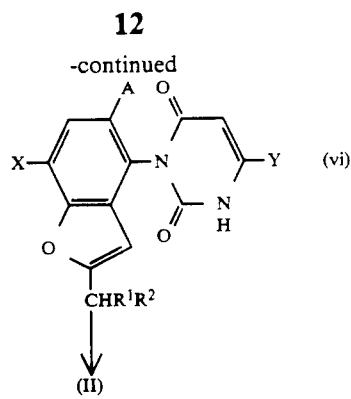

wherein $R^1$, $R^2$, A, X and Y are each as defined above.

The following will describe the respective steps in the above reaction scheme.

The compound (i) can be produced from the corresponding phenol by the method as described in EP-B 61 741.

The compound (ii) can be produced by heating the compound (i) with or 7ithout an inert solvent at a temperature of about 100° to 300° C., preferably about 150° to 250° C., for a period of about 2 to 100 hours.

Examples of the inert solvent are aromatic hydrocarbons such as toluene, xylene, mesitylene and tetraline; and tertiary amines such as N,N-diethylaniline. These solvents may be used solely or in any combination.

After completion of the reaction, the reaction mixture may be subjected to ordinary post-treatment. F/r instance, the reaction mixture is extracted 7ith an organic solvent, followed by concentration. If desired, any conventional purification procedure such as chromatography, distillation or recrystallization may be applied to the resulting product, thus obtaining the desired compound.

The compound (iii) can be produced by reacting the compound (ii) in the presence of an acid.

The reaction is usually carried out with or 7ithout an inert solvent at a temperature of about 0° to 100° C., preferably about 5° to 80° C., for a period of about 0.5 to 24 hours. The acid is used in an amount of 1.1 to 100 equivalents to one equivalent of the compound (ii).

Examples of the acid are inorganic acids such as hydrochloric acid, sulfuric acid and polyphosphoric acid; sulfonic acids such as p-toluenesulfonic acid and trifluoromethanesulfonic acid; and carboxylic acids such as formic acid, acetic acid and trifluoroacetic acid.

Examples of the inert solvent are aromatic hydrocarbons such as benzene and toluene; halogenated hydrocarbons such as chloroform, carbon tetrachloride; inorganic acid such as hydrochloric acid and sulfuric acid; organic acids such as acetic acid; and 7ater. These solvents may be used solely or in combination.

After completion of the reaction, the reaction mixture is subjected to ordinary post-treatment. F/r instance, the reaction mixture is poured into water, and the precipitated crystals are collected by filtration or the resultant mixture is extracted 7ith an organic solvent, followed by concentration. If desired, any conventional purification procedure such as chromatography or recrystallization may be applied to the resulting product, thus obtaining the desired compound.

The compound (iv) can be produced by reacting the compound (iii) 7ith methyl chlorocarbonate.

The reaction is carried out in an inert solvent in the presence of a base at a temperature of about 0° to 120°

C., preferably about 20° to 80° C., for a period of about 0.5 to 5 hours. The methyl chlorocarbonate and the base are used in amounts of 1 to 2 equivalents and of 1 to 1.5 equivalents to one equivalent of the compound (iii).

Examples of the base are organic bases such as triethylamine, pyridine and N,N-diethylaniline; and inorganic bases such as potassium carbonate and sodium hydride.

Examples of the inert solvent are aromatic hydrocarbons such as benzene and toluene; halogenated hydrocarbons such as chloroform and carbon tetrachloride; ethers such as diethyl ether, dioxane and tetrahydrofuran; ketones such as acetone and methyl isobutyl ketone; acid amines such as N,N-dimethylformamide; and sulfur compounds such as dimethylsulfoxide. These solvents may be used solely or in combination.

After completion of the reaction, the reaction mixture is subjected to ordinary post-treatment. F/r instance, the reaction mixture is poured into water, and the precipitated crystals are collected by filtration or the resultant mixture is extracted 7ith an organic solvent, followed by concentration. If desired, any conventional purification procedure such as chromatography or recrystallization may be applied to the resulting product, thus obtaining the desired compound.

The compound (v) can be produced by reacting the compound (iii) with phosgene.

The reacti/n is usually carried out in an inert solvent at a temperature of about 0° to 120° C., preferably about 20° to 100° C., for a period of about 0.5 to 12 hours. The phosgene is used in an amount of 2 to 10 equivalents to one equivalent of the compound (iii).

Examples of the inert solvent are aliphatic hydrocarbons such as hexane and heptane; aromatic hydrocarbons such as benzene and toluene; and halogenated hydrocarbons such as chloroform and carbon tetrachloride. These solvents may be used solely or in combination.

After completion of the reaction, the inert solvent and excess phosgene are removed from the reaction mixture, followed by purification, if necessary, 7ith a conventional technique such as distillation or recrystallization, thus obtaining the desired compound.

The compound (vi) can be obtained by reacting the compound (iv) 7ith a compound of the general formula:

$$Y(NH_2)C=CHCO_2C_2H_5 \qquad (vii)$$

7herein Y is as defined above.

The reaction is usually carried out in an inert solvent in the presence of a base at a temperature of about 0° to 150° C., preferably about 80° to 120° C., for a period of about 0.5 to 10 hours. The compound (vii) and the base are used in amounts of 1 to 10 equivalents and of 1 to 10 equivalents, respectively, to one equivalent of the compound (iv).

Examples of the base are inorganic bases such as sodium hydride and potassium hydride.

Examples of the inert solvent are aliphatic hydrocarbons such as hexane and heptane; aromatic hydrocarbons such as benzene and toluene; ethers such as diethyl ether, dioxane and tetrahydrofuran; acid amides such as N,N-dimethylformamide; and sulfur compounds such as dimethylsulfoxide. These solvents may be used solely or in combination.

After completion of the reaction, the reaction mixture is subjected to ordinary post-treatment. F/r instance, the reaction mixture is poured into 7ater or an acidic dilution, and the precipitated crystals are collected by filtration or extracted with an organic solvent, followed by concentration. If desired, any conventional purification procedure such as chromatography, distillation or recrystallization may be applied to the resulting product.

The compound (vi) can also be produced by reacting the compound (v) 7ith the compound (vii).

The reaction is usually carried out in an inert solvent in the presence of a base at a temperature of about 0° to 60° C., preferably about 5° to 30° C., for a period of about 0.5 to 10 hours. The compound (vii) and the base are used in amounts of 1 to 1.5 equivalents and of 1 to 1.5 equivalents, respectively, to one equivalent of the compound (v).

Examples of the base are inorganic bases such as sodium hydride and potassium hydride.

Examples of the inert solvent are aliphatic hydrocarbons such as hexane and heptane; aromatic hydrocarbons such as benzene and toluene; ethers such as diethyl ether, dioxane and tetrahydrofuran; acid amides such as N,N-dimethylformamide; and sulfur compounds such as dimethylsulfoxide. These solvents may be used solely or in any combination.

After completion of the reaction, the reaction mixture is subjected to ordinary post-treatment. F/r instance, the reaction mixture is poured into water or an acidic dilution, and the precipitated crystals are collected by filtration or extracted 7ith an organic solvent, followed by concentration. If desired, any conventional purification procedure such as chromatography, distillation or recrystallization may be applied to the resulting product.

The compound (II) can be produced by reacting the compound (vi) 7ith a compound of the formula:

$$CH_3—D \qquad (viii)$$

7herein D is halogen such as chlorine, bromine or iodine; or methanesulfonyloxy; or alternatively, with a compound of the formula:

$$NH_2—E \qquad (ix)$$

wherein E is methanesulfonyloxy, p-toluenesulfonyloxy or 2,4-dinitrophenoxy.

The reaction is usually carried out in an inert solvent in the presence of a base at a temperature of about 0° to 100° C. for a period of about 0.5 to 10 hours. The compound (viii) or (ix) and the base are used in amounts of 1 to 10 equivalents and of 1 to 1.5 equivalents, respectively, to one equivalent of the compound (vi).

Examples of the base are inorganic bases such as sodium hydride and potassium hydride; and alkaline metal alkoxides such as sodium methoxide and sodium ethoxide.

Examples of the inert solvent are aliphatic hydrocarbons such as hexane and heptane; aromatic hydrocarbons such as benzene, toluene and xylene; halogenated hydrocarbons such as chloroform and carbon tetrachloride; ethers such as diethyl ether, dioxane and tetrahydrofuran; ketones such as acetone and methyl isobutyl ketone; esters such as ethyl acetate; acid amines such as N,N-dimethylformamide; and sulfur compounds such as dimethylsulfoxide. These solvents may be used solely or in any combination.

After completion of the reaction, the reaction mixture is subjected to ordinary post-treatment. F/r instance, the reaction mixture is poured into water, and the precipitated crystals are collected by filtration or the resultant mixture is extracted with an organic solvent, followed by concentration. If desired, any conventional purification procedure such as chromatography or recrystallization may be applied to the resulting product, thus obtaining the desired compound.

The compounds (I) of the present invention have excellent herbicidal activity and excellent selectivity between crop plants and weeds. In other words, the compounds (I) of the present invention can exhibit herbicidal activity against various unfavorable weeds under the foliar treatment or soil treatment on upland fields. The compounds (I) of the present invention can also exhibit herbicidal activity against various unfavorable weeds under the flooding treatment on paddy fields.

Examples of the weeds which can be controlled or exterminated by the compounds (I) of the present invention are broad-leaved weeds such as wild buckwheat (Polygonum convolvulus), pale smartweed (Polygonum lapathifolium), common purslane (Portulaca oleracea), common chickweed (Stellaria media), common lambsquarters (Chenopodium album), redroot pigweed (Amaranthus retroflexus), radish (Raphanus sativus), wild mustard (Sinapis arvensis), shepherdspurse (Capsella bursa-pastoris), hemp sesbania (Sesbania exaltata), sicklepod (Cassia obtusifolia), velvetleaf (Abutilon theophrasti), prickly sida (Sida spinosa), field pansy (Viola arvensis), catchweed bedstraw (Galium aparine), ivyleaf morningglory (Ipomoea hederacea), tall morningglory (Ipomoea purpurea), field bindweed (C/nvolvulus arvensis), purple deadnettle (Lamium purpureum), henbit (Lamium amplexicaure), Jimsonweed (Datura stramonium), black nightshade (Solanum nigrum), Persian speedwell (Veronica persica), common cocklebur (Xanthium pensylvanicum), common sunflower (Helianthus annuus), scentless chamomile (Matricaria perforata), corn marigold (Chrysanthemum segetum), sun spurge (Euphorbia helioscopia) and spotted spurge (Euphorbia maculata); gramineous weeds such as Japanese millet (Echinochloa frumentacea), barnyardgrass (Echinochloa crus-galli), green foxtail (Setaria viridis), southern crabgrass (Digitaria ciliaris), annual bluegrass (Poa annua), blackgrass (Alopecurus myosuroides), oats (Avena sativa), wild oats (Avena fatua), J/hnsongrass (Sorghum halepense), quackgrass (Agropyron repens), downy brome (Bromus tectorum), bermudagrass (Cynodon dactylon) and giant foxtail (Setaria faberi); commelinaceous weeds such as Asiatic dayflower (C/mmelina communis); and cyperaceous weeds such as rice flatsedge (Cyperus iria) and purple nutsedge (Cyperus rotundus). Some of the compounds (I) of the present invention exhibit no material phytotoxicity on main crops such as corn, wheat, barley, rice plant, soybean and cotton.

The particular compounds (I) of the present invention wherein R is carboxy or $C_1$-$C_5$ alkoxycarbonyl can exhibit excellent selectivity between corn and weeds such as morningglories, velvetleaf and black nightshade, as well as between wheat and undesired weeds such as Persian speedwell, wild buckwheat and catchweed bedstraw, under the soil treatment of upland fields. Moreover, the particular compounds (I) of the present invention wherein R is hydroxy($C_1$-$C_5$)alkyl, ($C_1$-$C_5$)acyloxy($C_1$-$C_5$)alkyl or ($C_1$-$C_5$)alkoxy($C_1$-$C_5$)alkyl can exhibit excellent selectivity between cotton and undesired weeds such as morningglories, black nightshade and giant foxtail, under the soil treatment of upland fields.

Some of the compounds (I) of the present invention have herbicidal activity against various unfavorable weeds under the flooding treatment on paddy fields, examples of which are gramineous weeds such as barnyard-grass (Echinochloa oryzicola); broad-leaved weeds such as common falsepimpernel (Lindernia procumbens), Indian toothcup (Rotala indica) and waterwort (Elatine triandra); cyperaceous weeds such as small flower umbrella sedge (Cyperus difformis), hardstem bulrush (Scirpus juncoides), needle spikerush (Eleocharis acicularis), and water nutgrass (Cyperus serotinus); and others such as monochoria (Monochoria vaginalis) and arrowhead (Sagittaria pygmaea), while they exhibit no material phytotoxicity on rice plant.

When the compound (I) of the present invention is used as an active ingredient of herbicides, it is usually formulated with solid or liquid carriers or diluents as well as surfactants and other auxiliary agents into conventional formulations such as emulsifiable concentrates, wettable powders, flowables, granules and water-dispersible granules.

These formulations contain the compound (I) as an active ingredient at a content within the range of from 0.001% to 80% by weight, preferably from 0.003% to 70% by weight, based on the total weight of each of the formulations.

Examples of the solid carrier or diluent are fine powders or granules of kaolin clay, attapulgite clay, bentonite, terra alba, pyrophyllite, talc, diatomaceous earth, calcite, walnut shell powders, urea, ammonium sulfate and synthetic hydrous silicate. As the liquid carrier or diluent, there can be exemplified aromatic hydrocarbons such as xylene and methylnaphthalene; alcohols such as isopropanol, ethylene glycol and 2-ethoxyethanol; ketones such as acetone, cyclohexanone and isophorone; vegetable oils such as soybean oil and cotton seed oil; and dimethylsulfoxide, N,N-dimethylformamide, acetonitrile, water and the like.

Examples of the surfactant used for emulsification, dispersing or spreading are those of anionic type, such as alkylsulfates, alkylsulfonates, alkylarylsulfonates, dialkylsulfosuccinates and phosphates of polyoxyethylene alkylaryl esters; and those of nonionic type, such as polyoxyethylene alkyl ethers, polyoxyethylene alkylaryl ethers, polyoxyethylene polyoxypropylene block copolymers, sorbitan fatty acid esters and polyoxyethylene sorbitan fatty acid esters.

Examples of the auxiliary agent are ligninsulfonates, alginates, polyvinyl alcohol, gum arabic, carboxymethyl cellulose (CMC) and isopropyl acid phosphate (PAP).

The compound (I) of the present invention is usually formulated in any suitable formulation and used for pre-emergence or post-emergence control of undesired weeds by the soil or foliar treatment for upland fields and by the flooding treatment for paddy fields. The soil treatment includes soil surface treatment and soil incorporation. The foliar treatment is effected by application over the plants or by directed application to the weeds to keep any chemical off the crop foliage.

Further, the compound (I) of the present invention may be used together with any other herbicide to enhance its herbicidal activity. Moreover, it may also be used in admixture with insecticides, acaricides, nematocides, fungicides, plant growth regulators, fertilizers, soil improver and the like.

The compound (I) of the present invention can be used as an active ingredient of herbicides to be employed for paddy fields, upland fields, orchards, pasturelands, lawns, forests and non-agricultural fields.

The compound (I) of the present invention can also be used as an active ingredient of harvestaid agents such as defoliants and desiccating agents for crop plants such as cotton (*Gossypium hirsutum*) and potato (*Solanum tuberosum*).

When the compound (I) of the present invention is used as an active ingredient of herbicides, the dosage thereof is usually in the range of from 0.001 to 80 grams, preferably from 0.01 to 20 grams, per are, although it may vary depending on the prevailing weather conditi/ns, formulation type employed, application timing, type of application, soil involved, crop and 7eed species, and the like. A designated amount of the compound (I) formulated in the form of an emulsifiable concentrate, 7ettable powder, flowable or the like, may usually be employed by diluting it 7ith 7ater at a volume of about 1 to 10 liters per are, if necessary, 7ith addition of an adjuvant such as a spreading agent. The compound (I) formulated in the form of a flowable or granules may usually be applied 7ithout dilution.

Examples of the adjuvant include, in addition to the surfactants as described above, polyoxyethylene resin acids (esters), ligninsulfonates, abietates, dinaphthylmethanedisulfonates, crop oil concentrates and crop oils such as soybean oil, corn oil, cotton seed oil and sunflower /il.

The present invention 7ill be further illustrated by the following production examples, formulation examples and test examples, which are not to be construed to limit the scope thereof.

The following will describe production examples 7herein the compounds of the present invention are designated by the corresponding numbers as shown in Table 1.

PRODUCTION EXAMPLE 1

Preparation of C/mpound Nos. 32, 33 and 34

A suspension of -bromosuccinimide (28.4 g), α,α'-azobisisobutyronitrile (0.1 g) and benzoyl peroxide (0.1 g) in carbon tetrachloride (200 ml) 7as heated to 80° C., to 7hich a solution of 1-(7-chloro-5-fluoro-2-methylbenzo[b]furan-4-yl)-3-methyl-4-trifluoromethyl-1,2,3,6-tetrahydropyrimidin-2,6-dione (10.0 g) in carbon tetrachloride (50 ml) 7as added dropwise over 1 hour, and the mixture 7as refluxed for 24 hours. After completion of the reaction, the reaction mixture was cooled to room temperature, and the precipitate 7as filtered and 7ashed with chloroform. The filtrate was combined 7ith the 7ash liquid, and the combined mixture 7as concentrated. The residue 7as fractioned and purified by silica gel chromatography 7ith hexane-ethyl acetate (4:1) to give C/mpound No. 32 (3.4 g), C/mpound No. 33 (8.8 g) and C/mpound No. 34 (1.1 g).

C/mpound /. 32: m.p., 174°–176° C.; $^1$H-NMR δ(ppm) [60 MHz, CDCl$_3$] 3.53 (3H, s), 4.47 (2H, s), 6.32 (1H, s), 6.56 (1H, s), 7.21 (1H, d, J=10 Hz).

C/mpound No. 33: $^1$H-NMR δ(ppm) [60 MHz, CDCl$_3$] 3.53 (3H, s), 6.32 (1H, s), 6.58 (1H, s), 6.74 (1H, s), 7.25 (1H, d, J=10 Hz).

C/mpound No. 34: $^1$H-NMR δ(ppm) [60 MHz, CDCl$_3$]3.57 (3H, s), 6.36 (1H, s), 6.97 (1H, s), 7.32 (1H, d, J=10 Hz).

PRODUCTION EXAMPLE 2

Preparation of C/mpound No. 1

1-(7-Chloro-2-dibromomethyl-5-fluorobenzo[b]furan-4-yl)-3-methyl-4-trifluoromethyl-1,2,3,6-tetrahydropyrimidin-2,6-dione (5.3 g) 7as added to concentrated sulfuric acid (20 ml), and the mixture 7as stirred at 50° C. for 1 hour. After completion of the reaction, the reaction mixture 7as poured into ice-water and extracted 7ith ethyl acetate (200 ml). The extract 7as 7ashed with saturated aqueous sodium hydrogencarbonate, dried and concentrated. The resulting crystals 7ere 7ashed 7ith hexane (30 ml) to give C/mpound No. 1 (2.9 g).

m.p., 204°–207° C.;
$^1$H-NMR δ(ppm) [60 MHz, CDCl$_3$]: 3.58 (3H, s), 6.37 (1H, s), 7.33 (1H, s), 7.44 (1H, d, J=10 Hz), 9.88 (1H, s).

PRODUCTION EXAMPLE 3

Preparation of C/mpound No. 2

1-(7-Chloro-5-fluoro-2-tribromomethylbenzo[b]furan-4-yl)-3-methyl-4-trifluoromethyl-1,2,3,6-tetrahydropyrimidin-2,6-dione (0.37 g) 7as added to concentrated sulfuric acid (2 ml), and the mixture 7as stirred at 45° C. for 3 hour. After completion of the reaction, the reaction mixture 7as poured into ice-water and extracted 7ith ethyl acetate (100 ml). The extract 7as washed 7ith 7ater, dried and concentrated to give C/mpound No. 2 (0.22 g).

$^1$H-NMR δ(ppm) [60 MHz, DMSO-d$_6$]: 3.25 (3H, s), 5.5–6.5 (1H, br), 6.39 (1H, s), 7.68 (1H, d, J=10 Hz), 7.78 (1H, s).

PRODUCTION EXAMPLE 4

Preparation of C/mpound No. 3

To a solution of 1-(7-chloro-5-fluoro-2-formylbenzo[b]furan-4-yl)-3-methyl-4-trifluoromethyl-1,2,3,6-tetrahydropyrimidin-2,6-dione (1.1 g) dissolved in tetrahydrofuran (20 ml), a 0.94N solution (3.1 ml) of diisobutylaluminum hydride in hexane was added at 5° C. over 5 minutes, and the mixture 7as then stirred at room temperature for 1 hour. After completion of the reaction, the reaction mixture was poured into water and extracted 7ith ethyl acetate (100 ml). The extract 7as 7ashed with 7ater, dried and concentrated. The residue 7as purified by silica gel chromatography 7ith hexane-ethyl acetate (1:1) to give C/mpound No. 3 (0.9 g).

m.p., 185°–187° C.;
$^1$H-NMR δ(ppm) [60 MHz, CDCl$_3$]: 3.32 (3H, s), 4.70 (2H, s), 6.33 (1H, s), 6.49 (1H, s), 7.20 (1H, d, J=10 Hz); IR ν cm$^{-1}$ 3300 (—OH).

PRODUCTION EXAMPLE 5

Preparation of C/mpound No. 4

To a solution of 1-(7-chloro-5-fluoro-2-formylbenzo[b]furan-4-yl)-3-methyl-4-trifluoromethyl-1,2,3,6-tetrahydropyrimidin-2,6-dione (0.38 g) dissolved in tetrahydrofuran (10 ml), an 1.0N solution (1.1 ml) of methylmagnesium bromide in tetrahydrofuran was added at −70° C. over 5 minutes, and the mixture was then stirred at room temperature for 1 hour. A&ter completion of the reaction, the reaction mixture was poured into 7ater and extracted 7ith ethyl acetate (100 ml). The extract 7as washed 7ith water, dried and concentrated. The residue 7as purified by silica gel chromatography with hexane-ethyl acetate (1:1) to give C/mpound No. 4 (0.13 g).

¹H-NMR δ(ppm) [60 MHz, CDCl₃]: 1.53 (3H, d, J=6 Hz), 2.5-3.0 (1H, br), 3.50 (3H, s), 4.86 (1H, q, J=6 Hz), 6.26 (1H, s), 6.40 (1H, s), 7.14 (1H, d, J=10 Hz).

PRODUCTION EXAMPLE 6

Preparation of C/mpound No. 5

1-(7-Chloro-5-fluoro-2-formylbenzo[b]furan-4-yl)-3-methyl-4-trifluoromethyl-1,2,3,6-tetrahydropyrimidin-2,6-dione (0.46 g) was dissolved in ethanol (10 ml), to which a solution of hydroxylamine hydrochloride (0.12 g) and sodium acetate (0.15 g) dissolved in water (5 ml) was added at room temperature, followed by stirring at 45° C. for 3 hours. After completion of the reaction, the reaction mixture was poured into water and extracted with ethyl acetate (100 ml). The extract was washed with water, dried and concentrated. The residue was purified by silica gel chromatography with hexane-ethyl acetate (1:1) to give C/mpound No. 5 (0.40 g).

¹H-NMR δ(ppm) [60 MHz, CDCl₃]: 3.56 (3H, s), 6.38 (1H, s), 6.77 (1H, s), 7.24 (1H, d, J=10 Hz), 7.96 (1H, s), 8.8-9.3 (1H, br).

PRODUCTION EXAMPLE 7

Preparation of C/mpound No. 8

1-(7-Chloro-5-fluoro-2-formylbenzo[b]furan-4-yl)-3-methyl-4-trifluoromethyl-1,2,3,6-tetrahydropyrimidin-2,6-dione (0.51 g) and hydroxylamine hydrochloride (0.11 g) were dissolved in N,N-dimethylformamide (10 ml), and the solution was refluxed for 3 hours. After completion of the reaction, the reaction mixture was poured into water and extracted with diethyl ether (100 ml). The extract was washed with water, dried and concentrated. The residue was purified by silica gel chromatography with hexane-ethyl acetate (4:1) to give C/mpound No. 8 (0.11 g).

m.p., 180°-182° C.;

¹H-NMR δ(ppm) [60 MHz, CDCl₃]: 3.54 (3H, s), 6.32 (1H, s), 7.21 (1H, s), 7.39 (1H, d, J=10 Hz).

PRODUCTION EXAMPLE 8

Preparation of C/mpound No. 11

1-(7-Chloro-5-fluoro-2-hydroxymethylbenzo[b]furan-4-yl)-3-methyl-4-trifluoromethyl-1,2,3,6-tetrahydropyrimidin-2,6-dione (0.20 g) and 4-dimethylaminopyridine (10 mg) were dissolved in pyridine (2 ml), to which acetic anhydride (0.06 g) was added, and the mixture was stirred at room temperature for 2 hours. After completion of the reaction, the reaction mixture was poured into water and extracted with diethyl ether (100 ml). The extract was washed with 2% hydrochloric acid, dried and concentrated. The residue was purified by silica gel chromatography with hexane-ethyl acetate (2:1) to give C/mpound No. 11 (0.22 g).

¹H-NMR δ(ppm) [60 MHz, CDCl₃]: 2.07 (3H, s), 3.52 (3H, s), 5.10 (2H, s), 6.30 (1H, s), 6.54 (1H, s) 7.16 (1H, d, J=10 Hz).

PRODUCTION EXAMPLE 9

Preparation of C/mpound No. 12

1-[7-Chloro-5-fluoro-2-(1-hydroxyethyl)benzo[b]furan-4-yl]-3-methyl-4-trifluoromethyl-1,2,3,6-tetrahydropyrimidine-2,6-dione (0.19 g) was dissolved in acetone (5 ml), to which J/nes reagent (a mixed solution of chromium trioxide, sulfuric acid and water; see Organic Synthesis col. Vol. 1) was added at 5° C., until the orange color of chromium trioxide did not become disappeared. After completion of the reaction, the reaction mixture was poured into water and extracted with ethyl acetate (100 ml). The extract was washed with water, dried and concentrated. The residue was purified by silica gel chromatography with hexane-ethyl acetate (2:1) to give C/mpound No. 12 (0.11 g).

¹H-NMR δ(ppm) [60 MHz, CDCl₃]: 2.60 (3H, s), 3.55 (3H, s), 6.35 (1H, s), 7.22 (1H, s), 7.38 (1H, d, J=10 Hz).

PRODUCTION EXAMPLE 10

Preparation of C/mpound No. 13

To a solution of 1-[7-chloro-5-fluoro-2-(1-hydroxyethyl)benzo[b]furan-4-yl]-3-methyl-4-trifluoromethyl-1,2,3,6-tetrahydropyrimidin-2,6-dione (0.20 g) dissolved in N,N-dimethylformamide (5 ml), sodium hydride (0.02 g) was added at room temperature. After stirring at room temperature for 10 minutes, methyl iodide (0.5 ml) was added thereto, and the mixture was further stirred at room temperature for 2 hours. After completion of the reaction, the reaction mixture was poured into water and extracted with ethyl acetate (100 ml). The extract was washed with water, dried and concentrated. The residue was purified by silica gel chromatography with hexane-ethyl acetate (2:1) to give C/mpound No. 13 (0.05 g).

¹H-NMR δ(ppm) [60 MHz, CDCl₃]: 1.54 (3H, d, J=6 Hz), 3.34 (3H, s), 3.54 (3H, s), 4.45 (1H, q, J=6 Hz), 6.33 (1H, s), 6.44 (1H, s), 7.17 (1H, d, J=10 Hz).

PRODUCTION EXAMPLE 11

Preparation of C/mpound /. 14

To a solution of 1-[7-chloro-5-fluoro-2-(1-hydroxyethyl)benzo[b]furan-4-yl]-3-methyl-4-trifluoromethyl-1,2,3,6-tetrahydropyrimidin-2,6-dione (0.20 g) and 4-dimethylaminopyridine (10 mg) dissolved in pyridine (2 ml), acetic anhydride (0.06 g) was added, and the mixture was then stirred at room temperature for 2 hours. After completion of the reaction, the reaction mixture was poured into water and extracted with diethyl ether (100 ml). The extract was washed with 2% hydrochloric acid, dried and concentrated. The residue was purified by silica gel chromatography with hexane-ethyl acetate (2:1) to give C/mpound /. 14 (0.20 g).

¹H-NMR δ(ppm) [60 MHz, CDCl₃]: 1.64 (3H, d, J=6 Hz), 2.05 (3H, s), 3.55 (3H, s), 6.01 (1H, q, J=6 Hz), 6.35 (1H, s), 6.51 (1H, s), 7.21 (1H, d, J=10 Hz).

PRODUCTION EXAMPLE 12

Preparation of C/mpound No. 16

To a solution of 1-(2-carboxy-7-chloro-5-fluorobenzo[b]furan-4-yl)-3-methyl-4-trifluoromethyl-1,2,3,6-tetrahydropyrimidin-2,6-dione (0.24 g) dissolved in methanol (5 ml), a diethyl ether solution of diazomethane which had been prepared from nitrosodimethyl urea was added at 0° C., until no formation of nitrogen gas was observed. After completion of the reaction, the reaction mixture was concentrated, and the residue was purified by silica gel chromatography with hexane-ethyl acetate (2:1) to give C/mpound No. 16 (0.21 g).

m.p., 184°-186° C.;

¹H-NMR δ(ppm) [60 MHz, CDCl₃]: 3.55 (3H, s), 3.92 (3H, s), 6.33 (1H, s), 7.30 (1H, s), 7.37 (1H, d, J=10 Hz).

PRODUCTION EXAMPLE 13

Preparation of C/mpound No. 17

1-(2-Carboxy-7-chloro-5-fluorobenzo[b]furan-4-yl)-3-methyl-4-trifluoromethyl-1,2,3,6-tetrahydropyrimidin-2,6-dione (0.22 g) and p-toluenesulfonic acid monohydrate (10 mg) 7ere dissolved in ethanol (5 ml), and the solution 7as refluxed for 3 hours. After completion of the reaction, the reaction mixture 7as concentrated, and the residue 7as purified by silica gel chromatography 7ith hexane-ethyl acetate (2:1) to give C/mpound No. 17 (0.13 g).

$^1$H-NMR δ(ppm) [60 MHz, CDCl$_3$[: 1.39 (3H, t, J=7 Hz), 3.56 (3H, s), 4.40 (2H, q, J=7 Hz), 6.35 (1H, s), 7.31 (1H, s), 7.38 (1H, d, J=10 Hz).

PRODUCTION EXAMPLE 14

Preparation of C/mpound No. 18

1-(2-Carboxy-7-chloro-5-fluorobenzo[b]furan-4-yl)-3-methyl-4-trifluoromethyl-1,2,3,6-tetrahydropyrimidin-2,6-dione (0.20 g) and p-toluenesulfonic acid monohydrate (10 mg) were dissolved in 2-propanol (2 ml), and the solution 7as refluxed for 6 hours. After completion of the reaction, the reaction mixture 7as cooled to room temperature and purified by silica gel chromatography 7ith hexane-ethyl acetate (2:1) to give C/mpound No. 18 (0.06 g).

$^1$H-NMR δ(ppm) [60 MHz, CDCl$_3$]: 1.38 (6H, d, J=6 Hz), 3.56 (3H, s), 5.25 (1H, m), 6.37 (1H, s), 7.26 (1H, s), 7.37 (1H, d, J=10 Hz).

PRODUCTION EXAMPLE 15

Preparation of C/mpound No. 19

1-(2-Carboxy-7-chloro-5-fluorobenzo[b]furan-4-yl)-3-methyl-4-trifluoromethyl-1,2,3,6-tetrahydropyrimidin-2,6-dione (0.10 g) and p-toluenesulfonic acid monohydrate (10 mg) 7ere dissolved in 1-pentanol (2 ml), and the solution 7as stirred at 100° C. for 1 hour. After completion of the reaction, the reaction mixture was cooled to room temperature and purified by silica gel chromatography 7ith hexane-ethyl acetate (2:1) to give C/mpound No. 19 (0.08 g).

$^1$H-NMR δ(ppm) [60 MHz, CDCl$_3$]: 0.92 (3H, t, J=6 Hz), 1.1–1.9 (6H, m), 3.54 (3H, s), 4.32 (2H, t, J=6 Hz), 6.32 (1H, s), 7.25 (1H, s), 7.33 (1H, d, J=10 Hz).

PRODUCTION EXAMPLE 16

Preparation of C/mpound No. 20

To a solution of 1-(2-carboxy-7-chloro-5-fluorobenzo[b]furan-4-yl)-3-methyl-4-trifluoromethyl-1,2,3,6-tetrahydropyrimidin-2,6-dione (0.30 g) dissolved in dichloromethane (5 ml), thionyl chloride (0.13 g) was added dropwise at room temperature. After refluxing for 3 hours, the mixture 7as concentrated and thionyl chloride 7as distilled off. To the residue, dichloromethane (5 ml) 7as added, and the mixture 7as stirred at 5° C. for 1 hour, 7hile introducing a stream of ammonia to pass thereinto. After completion of the reaction, the reaction mixture 7as poured into 7ater and extracted with ethyl acetate (100 ml). The extract 7as washed with 7ater, dried and concentrated. The residue 7as purified by silica gel chromatography with hexane-ethyl acetate (1:1) to give C/mpound No. 20 (0.06 g).

$^1$H-NMR δ(ppm) [60 MHz, CDCl$_3$]: 3.56 (3H, s), 5.8–6.8 (2H, br), 6.37 (1H, s), 7.32 (1H, s), 7.34 (1H, d, J=10 Hz).

PRODUCTION EXAMPLE 17

Preparation of C/mpound Nos. 35, 36 and 37

N-bromosuccinimide (10.1 g), α,α'-azobisisobutyronitrile (0.1 g) and benzoyl peroxide (0.1 g) 7ere suspended in carbon tetrachloride (150 ml), and the suspension 7as heated to 80° C. To this suspension, a solution of 1-(5,7-difluoro-2-methylbenzo[b]furan-4-yl)-3-methyl-4-trifluoromethyl-1,2,3,6-tetrahydropyrimidin-2,6-dione (4.5 g) dissolved in carbon tetrachloride (30 ml) was added dropwise /ver 30 minutes, and the mixture was refluxed for 12 hours. After completion of the reaction, the reaction mixture 7as poured into 7ater and extracted with ethyl acetate (300 ml). The extract 7as 7ashed 7ith water, dried and concentrated. The residue was fractioned and purified by silica gel chromatography 7ith hexane-ethyl acetate (4:1) to give C/mpound No. 35 (0.85 g), C/mpound No. 36 (3.0 g) and C/mpound No. 37 (0.96 g).

C/mpound No. 35: $^1$H-NMR δ(ppm) [60 MHz, CDCl$_3$]3.60 (3H, s), 4.51 (2H, s), 6.39 (1H, s), 6.60 (1H, d, J=2 Hz), 7.01 (1H, t, J=10 Hz).

C/mpound No. 36: $^1$H-NMR δ(ppm) [60 MHz, CDCl$_3$]3.61 (3H, s), 6.41 (1H, s), 6.63 (1H, s), 6.80 (1H, d, J=2 Hz), 7.10 (1H, t, J=10 Hz).

C/mpound No. 37; $^1$H-NMR δ(ppm) [60 HMz, CDCl$_3$]3.58 (3H, s), 6.37 (1H, s), 7.00 (1H, d, J=2 Hz), 7.10 (1H, t, J=10 Hz).

PRODUCTION EXAMPLE 18

Preparation of C/mpound /. 22

1-(2-Dibromomethyl-5,7-difluorobenzo[b]furan-4-yl)-3-methyl-4-trifluoromethyl-1,2,3,6-tetrahydropyrimidin-2,6-dione (2.3 g) was added to concentrated sulfuric acid (8 ml), and the mixture 7as stirred at 50° C. for 2 hours. After completion of the reaction, the reaction mixture was poured into ice-water and extracted 7ith ethyl acetate (100 ml). The extract was 7ashed 7ith saturated aqueous sodium hydrogencarbonate, dried and concentrated. The residue 7as purified by silica gel chromatography 7ith hexane-ethyl acetate (2:1) to give C/mpound /. 22 (1.2 g). m.p., 195°–197° C.;

$^1$H-NMR δ(ppm) [60 MHz, CDCl$_3$]: 3.60 (3H, s), 6.41 (1H, s), 7.23 (1H, t, J=10 Hz), 7.39 (1H, d, J=2 Hz), 9.90 (1H, s).

PRODUCTION EXAMPLE 19

Preparation of C/mpound No. 23

1-(5,7-Difluoro-2-tribromomethylbenzo[b]furan-4-yl)-3-methyl-4-trifluoromethyl-1,2,3,6-tetrahydropyrimidin-2,6-dione (0.64 g) 7as added to concentrated sulfuric acid (5 ml), and the mixture 7as stirred at 45° C. for 2 hours. After completion of the reaction, the reaction mixture was poured into ice-water and extracted with ethyl acetate (100 ml). The extract 7as washed 7ith water, dried and concentrated. The residue 7as 7ashed 7ith hexane (20 ml) to give C/mpound No. 23 (0.30 g).

$^1$H-NMR δ(ppm) [60 MHz, CDCl$_3$]: 3.61 (3H, s), 6.46 (1H, s), 7.19 (1H, t, J=10 Hz), 7.45 (1H, d, J=2 Hz), 8.4–8.6 (1H, br).

PRODUCTION EXAMPLE 20

Preparation of C/mpound No. 24

To a solution of 1-(5,7-difluoro-2-formylbenzo[b]furan-4-yl)-3-methyl-4-trifluoromethyl-1,2,3,6-tetrahydropyrimidin-2,6-dione (0.82 g) dissolved in tetrahydrofuran (20 ml), a 0.94N solution (2.8 ml) of diisobutylaluminum hydride (2.8 ml) in hexane was added dropwise at 5° C. over 5 minutes, and the mixture 7as stirred at 5° C. for 1 hour. After completion of the reaction, the reaction mixture 7as poured into 7ater and extracted 7ith ethyl acetate (100 ml). The extract 7as 7ashed with water, dried and concentrated. The residue was purified by silica gel chromatography 7ith hexane-ethyl acetate (1:1) to give C/mpound No. 24 (0.73 g). m.p., 171°-173° C.

¹H-NMR δ(ppm) [60 MHz, CDCl₃]: 3.35 (1H, t, J=6 Hz), 3.47 (3H, s), 4.52 (2H, d, J=6 Hz), 6.23 (1H, s), 6.37 (1H, d, J=2 Hz), 6.88 (1H, t, J=10 Hz).

PRODUCTION EXAMPLE 21

Preparation of C/mpound No. 25

To a solution of 1-(5,7-difluoro-2-formylbenzo[b]furan-4-yl)-3-methyl-4-trifluoromethyl-1,2,3,6-tetrahydropyrimidin-2,6-dione (0.77 g) dissolved in tetrahydrofuran (20 ml), an 1.0N solution (3.1 ml) of methylmagnesium bromide in tetrahydrofuran was added dropwise at −70° C. for 5 minutes, and the mixture 7as stirred at 0° C. for 2 hours. After completion of the reaction, the reaction mixture was poured into 7ater and extracted 7ith ethyl acetate (100 ml). The extract 7as washed 7ith 7ater, dried and concentrated. The residue was purified by silica gel chromatography with hexane-ethyl acetate (1:1) to give C/mpound No. 25 (0.52 g).

¹H-NMR δ(ppm) [60 MHz, CDCl₃]: 1.57 (3H, d, J=6 Hz), 2.61 (1H, d, J=6 Hz), 3.59 (3H, s), 4.8-5.1 (1H, m), 6.37 (1H, s), 6.47 (1H, d, J=2 Hz), 6.99 (1H, t, J=10 Hz).

PRODUCTION EXAMPLE 22

Preparation of C/mpound No. 27

1-(5,7-Difluoro-2-hydroxymethylbenzo[b]furan-4-yl)-3-methyl-4-trifluoromethyl-1,2,3,6-tetrahydropyrimidin-2,6-dione (0.12 g) and 4-dimethylaminopyridine (10 mg) 7ere dissolved in pyridine (2 ml), to 7hich acetic anhydride (0.05 g) 7as added, and the mixture 7as stirred at room temperature for 1 hour. After completion of the reaction, the reaction mixture 7as poured into water and extracted 7ith diethyl ether (100 ml). The extract 7as 7ashed 7ith 2% hydrochloric acid, dried and concentrated. The residue 7as purified by silica gel chromatography 7ith hexane-ethyl acetate (2:1) to give C/mpound No. 27 (0.11 g).

¹H-NMR δ(ppm) [60 MHz, CDCl₃]: 2.07 (3H, s), 3.51 (3H, s), 5.10 (2H, s), 6.29 (1H, s), 6.55 (1H, d, J=2 Hz), 6.95 (1H, t, J=10 Hz).

PRODUCTION EXAMPLE 23

Preparation of C/mpound /. 28

To a solution of 1-[5,7-difluoro-2-(1-hydroxyethyl)-benzo[b]furan-4-yl]-3-methyl-4-trifluoromethyl-1,2,3,6-tetrahydropyrimidin-2,6-dione (0.12 g) and 4-dimethylaminopyridine (10 mg) dissolved in pyridine (2 ml), acetic anhydride (0.05 g) 7as added, and the mixture 7as stirred at room temperature for 1 hour. After completion of the reaction, the reaction mixture 7as poured into water and extracted 7ith diethyl ether (100 ml). The extract 7as 7ashed 7ith 2% hydrochloric acid, dried and concentrated. The residue was purified by silica gel chromatography 7ith hexane-ethyl acetate (2:1) to give C/mpound No. 28 (0.13 g).

¹H-NMR δ(ppm) [60 MHz, CDCl₃]: 1.59 (3H, d, J=6 Hz), 2.01 (3H, s), 3.51 (3H, s), 5.98 (1H, q, J=6 Hz), 6.32 (1H, s), 6.49 (1H, d, J=2 Hz), 6.95 (1H, t, J=10 Hz).

PRODUCTION EXAMPLE 24

Preparation of C/mpound No. 29

To a solution of 1-[5,7-difluoro-2-(1-hydroxyethyl)-benzo[b]furan-4-yl)-3-methyl-4-trifluoromethyl-1,2,3,6-tetrahydropyrimidin-2,6-dione (0.25 g) dissolved in acetone (5 ml), J/nes reagent 7as added at −5° C., until the orange color of chromium trioxide did not become disappeared, and the mixture was stirred at room temperature for 2 hours. After completion of the reaction, the reaction mixture was poured into 7ater and extracted 7ith ethyl acetate (100 ml). The extract 7as washed 7ith 7ater, dried and concentrated. The residue was purified by silica gel chromatography 7ith hexane-ethyl acetate (2:1) to give Compound No. 29 (0.20 g).

¹H-NMR δ(ppm) [60 MHz, CDCl₃]: 2.61 (3H, s), 3.57 (3H, s), 6.37 (1H, s), 7.15 (1H, t, J=10 Hz), 7.25 (1H, d, J=2 Hz).

PRODUCTION EXAMPLE 25

Preparation of C/mpound No. 30

To a solution of 1-(2-carboxy-5,7-difluorobenzo[b]furan-4-yl)-3-methyl-4-trifluoromethyl-1,2,3,6-tetrahydropyrimidin-2,6-dione (0.15 g) dissolved in methanol (2 ml), a diethyl ether solution of diazomethane, which had been prepared from nitrosodimethyl urea, was added dropwise at 5° C., until no formation of nitrogen gas was observed. After completion of the reaction, the reaction mixture 7as concentrated, and the residue 7as purified by silica gel chromatography 7ith hexane-ethyl acetate (2:1) to give C/mpound /. 30 (0.13 g).

¹H-NMR δ(ppm) [60 MHz, CDCl₃]: 3.57 (3H, s), 3.94 (3H, s), 6.36 (1H, s), 7.12 (1H, t, J=10 Hz), 7.31 (1H, d, J=2 Hz).

PRODUCTION EXAMPLE 26

Preparation of C/mpound No. 31

1-(2-Carboxy-5,7-difluorobenzo[b]furan-4-yl)-3-methyl-4-trifluoromethyl-1,2,3,6-tetrahydropyrimidin-2,6-dione (0.10 g) and p-toluenesulfonic acid monohydrate (10 mg) 7ere dissolved in 1-pentanol (1 ml), and the solution 7as stirred at 100° C. for 1 hours. After completion of the reaction, the reaction mixture 7as cooled to room temperature and purified by silica gel chromatography with hexane-ethyl acetate (2:1) to give C/mpound No. 31 (0.10 g).

¹H-NMR δ(ppm) [60 MHz, CDCl₃]: 0.91 (3H, t, J=6 Hz), 1.0-2.0 (6H, m), 3.53 (3H, s), 4.32 (2H, t, J=6 Hz), 6.32 (1H, s), 7.08 (1H, t, J=10 Hz), 7.24 (1H, d, J=2 Hz).

The compounds (I) of the present invention 7hich were produced in the above production examples, together 7ith those 7hich can be produced in the same manner as described therein, are shown in Table 1.

TABLE 1

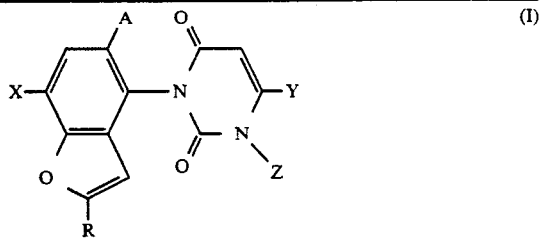

(I)

| Compound No. | A | X | Y | Z | R | Physical properties |
|---|---|---|---|---|---|---|
| 1 | F | Cl | $CF_3$ | $CH_3$ | CHO | m.p. 204–207° C. |
| 2 | F | Cl | $CF_3$ | $CH_3$ | COOH | |
| 3 | F | Cl | $CF_3$ | $CH_3$ | $CH_2OH$ | m.p. 185–187° C. |
| 4 | F | Cl | $CF_3$ | $CH_3$ | $CH(CH_3)OH$ | |
| 5 | F | Cl | $CF_3$ | $CH_3$ | CH=NOH | |
| 6 | F | Cl | $CF_3$ | $CH_3$ | $CH=NOCH_3$ | m.p. 153–155° C. |
| 7 | F | Cl | $CF_3$ | $CH_3$ | $CH=NOC_2H_5$ | m.p. 147–148.5° C. |
| 8 | F | Cl | $CF_3$ | $CH_3$ | CN | m.p. 180–182° C. |
| 9 | F | Cl | $CF_3$ | $CH_3$ | $CH_2OCH_2OCH_3$ | m.p. 95–98° C. |
| 10 | F | Cl | $CF_3$ | $CH_3$ | $CH_2OCH_3$ | m.p. 117–120° C. |
| 11 | F | Cl | $CF_3$ | $CH_3$ | $CH_2OC(O)CH_3$ | |
| 12 | F | Cl | $CF_3$ | $CH_3$ | $COCH_3$ | m.p. 194.5–195.5° C. |
| 13 | F | Cl | $CF_3$ | $CH_3$ | $CH(CH_3)OCH_3$ | |
| 14 | F | Cl | $CF_3$ | $CH_3$ | $CH(CH_3)OC(O)CH_3$ | |
| 15 | F | Cl | $CF_3$ | $CH_3$ | $C(CH_3)=NOH$ | m.p. 258–261° C. |
| 16 | F | Cl | $CF_3$ | $CH_3$ | $COOCH_3$ | m.p. 184–186° C. |
| 17 | F | Cl | $CF_3$ | $CH_3$ | $COOC_2H_5$ | m.p. 123.5–125.5° C. |
| 18 | F | Cl | $CF_3$ | $CH_3$ | $COOCH(CH_3)_2$ | m.p. 136–137.5° C. |
| 19 | F | Cl | $CF_3$ | $CH_3$ | $COOC_5H_{11}(n)$ | |
| 20 | F | Cl | $CF_3$ | $CH_3$ | $CONH_2$ | |
| 21 | F | Cl | $CF_3$ | $CH_3$ | $CH=N N(CH_3)_2$ | NMR data* |
| 22 | F | F | $CF_3$ | $CH_3$ | CHO | m.p. 195–197° C. |
| 23 | F | F | $CF_3$ | $CH_3$ | COOH | |
| 24 | F | F | $CF_3$ | $CH_3$ | $CH_2OH$ | m.p. 171–173° C. |
| 25 | F | F | $CF_3$ | $CH_3$ | $CH(CH_3)OH$ | |
| 26 | F | F | $CF_3$ | $CH_3$ | $CH_2OCH_3$ | NMR data* |
| 27 | F | F | $CF_3$ | $CH_3$ | $CH_2OC(O)CH_3$ | |
| 28 | F | F | $CF_3$ | $CH_3$ | $CH(CH_3)OC(O)CH_3$ | |
| 29 | F | F | $CF_3$ | $CH_3$ | $COCH_3$ | m.p. 184–185.5° C. |
| 30 | F | F | $CF_3$ | $CH_3$ | $COOCH_3$ | |
| 31 | F | F | $CF_3$ | $CH_3$ | $COOC_5H_{11}(n)$ | |
| 32 | F | Cl | $CF_3$ | $CH_3$ | $CH_2Br$ | |
| 33 | F | Cl | $CF_3$ | $CH_3$ | $CHBr_2$ | |
| 34 | F | Cl | $CF_3$ | $CH_3$ | $CBr_3$ | |
| 35 | F | F | $CF_3$ | $CH_3$ | $CH_2Br$ | |
| 36 | F | F | $CF_3$ | $CH_3$ | $CHBr_2$ | |
| 37 | F | F | $CF_3$ | $CH_3$ | $CBr_3$ | |
| 38 | F | Cl | $CF_2Cl$ | $CH_3$ | CHO | m.p. 188–190° C. |
| 39 | F | Cl | $CF_2Cl$ | $CH_3$ | $COOCH_3$ | m.p. 193–194.5° C. |
| 40 | F | Cl | $CF_2Cl$ | $CH_3$ | $COOC_5H_{11}(n)$ | m.p. 98–103° C. |
| 41 | F | Cl | $CF_2Cl$ | $CH_3$ | $CH_2OH$ | NMR data* |
| 42 | F | Cl | $CF_2Cl$ | $CH_3$ | $CH_2OC(O)CH_3$ | NMR data* |
| 43 | Cl | Cl | $CF_3$ | $CH_3$ | $COOCH_3$ | NMR data* |
| 44 | Cl | Cl | $CF_3$ | $CH_3$ | $COOC_5H_{11}(n)$ | m.p. 102–106° C. |
| 45 | Cl | Cl | $CF_3$ | $CH_3$ | $CH_2OC(O)CH_3$ | NMR data* |
| 46 | F | F | $CF_3$ | $CH_3$ | CH=NOH | m.p. 241–244° C. |
| 47 | F | F | $CF_3$ | $CH_3$ | $CH_2OC(O)CF_3$ | m.p. 164–166° C. |

*NMR data of the respective compounds are as follows.
Compound No. 21
$^1$H-NMR δ(ppm)[60MHz, $CDCl_3$]: 3.02(6H, s), 3.51(3H, s), 6.30(1H, s), 6.47(1H, s), 6.93(1H, s), 7.04(1H, d, J=10Hz).
Compound No. 26
$^1$H-NMR δ(ppm)[60MHz, $CDCl_3$]: 3.42(3H, s), 3.56(3H, s), 4.52(2H, s), 6.36(1H, s), 6.51(1H, d, J=2Hz), 7.01(1H, t, J=10Hz).
Compound No. 41
$^1$H-NMR δ(ppm)[60MHz, $CDCl_3$]: 3.0–3.4(1H, br), 3.60(3H, s), 4.65(2H, br), 6.24(1H, s), 6.48(1H, s), 7.19(1H, d, J=10Hz).
Compound No. 42
$^1$H-NMR δ(ppm)[60MHz, $CDCl_3$]: 2.06(3H, s), 3.62(3H, s), 5.20(2H, s), 6.36(1H, s), 6.70(1H, s), 7.33(1H, d, J=10Hz).
Compound No. 43
$^1$H-NMR δ(ppm)[60MHz, $CDCl_3$]: 3.57(3H, s), 3.94(3H, s), 6.35(1H, s), 7.29(1H, s), 7.60(1H, s).
Compound No. 45
$^1$H-NMR δ(ppm)[60MHz, $CDCl_3$]: 2.06(3H, s), 3.50(3H, s), 5.07(2H, s), 6.26(1H, s), 6.49(1H, s), 7.38(1H, s).

The following 7ill describe formulation examples wherein the compounds of the present invention are designated by the corresponding numbers as shown in Table 1 and parts are all by 7eight.

FORMULATION EXAMPLE 1

Fifty parts of any one of C/mpound Nos. 1–18, 20–25 and 28–30, 3 parts of calcium ligninsulfonate, 2 parts of sodium laurylsulfate and 45 parts of synthetic hydrous silicate are well mixed while being powdered to obtain a wettable powder.

FORMULATION EXAMPLE 2

Five parts of any one of C/mpound Nos. 1–47, 14 parts of polyoxyethylene styryl phenyl ether, 6 parts of calcium dodecylbenzenesulfonate, 25 parts of xylene and 50 parts of cyclohexanone are well mixed to obtain an emulsifiable concentrate.

FORMULATION EXAMPLE 3

Two parts of any one of C/mpound Nos. 1–31, 1 part of synthetic hydrous silicate, 2 parts of calcium lignin-sulfonate, 30 parts of bentonite and 65 parts of caoline clay are well mixed while being powdered. The mixture is then kneaded with water, granulated and dried to obtain granules.

FORMULATION EXAMPLE 4

Twenty five parts of any one of C/mpound /s. 1–18, 20–25 and 28–30, 3 parts of polyoxyethylene sorbitan monooleate, 3 parts of CMC and 69 parts of water are well mixed, and the mixture was then pulverized until the particle size thereof becomes not greater than 5 microns to obtain a flowable.

The following will describe test examples wherein the compounds of the present invention are designated by the corresponding numbers as shown in Table 1 and the compound used for comparison is designated by the symbol as shown in Table 2.

TABLE 2

| Symbol | Structure | Notes |
|---|---|---|
| A | (chemical structure: 4-chloro-2-fluoro-phenyl attached to N of a bicyclic imide with OCH$_2$CH$_3$ substituent) | Compound as disclosed in U.S. Pat. No. 4,881,967 |

The herbicidal activity on weeds and the phytotoxicity to crop plants were determined by visual observation as to the degree of germination and growth of the test plants (i.e., weeds and crop plants), and rated with an index 0, 1, 2, 3, 4 or 5, the numeral "0" indicating little or no material difference as seen in comparison with the untreated plants and the numeral "5" indicating the complete death of the test plants or the complete inhibition of their germination or growth.

TEST EXAMPLE 1

Cylindrical plastic pots (diameter, 10 cm; height, 10 cm) were filled with upland field soil, and the seeds of Japanese millet, tall morningglory and velvetleaf were sowed therein and covered with soil. A designated amount of the test compound formulated in an emulsifiable concentrate as described in F/rmulation Example 2 was diluted with water, and the dilution was sprayed onto the soil surface by means of a small sprayer at a spray volume of 10 liters per acre. The test plants were grown in a greenhouse for 19 days, and the herbicidal activity was examined. The results are shown in Table 3.

TABLE 3

| | | Herbicidal Activity | | |
|---|---|---|---|---|
| Compound No. | Dosage (g/are) | Japanese millet | Tall morning-glory | Velvet-leaf |
| 1 | 0.31 | 5 | 5 | 5 |
| 2 | 1.25 | 4 | 5 | 5 |
| 3 | 0.31 | 5 | 5 | 5 |
| 4 | 0.31 | 5 | 5 | 5 |
| 5 | 0.31 | 5 | 5 | 5 |
| 6 | 1.25 | 5 | 5 | 5 |
| 7 | 1.25 | 5 | 5 | 5 |
| 8 | 0.31 | 5 | 5 | 5 |
| 9 | 1.25 | 5 | 5 | 5 |
| 10 | 0.08 | 5 | 5 | 5 |
| 11 | 0.31 | 5 | 5 | 5 |
| 12 | 0.08 | 5 | 5 | 5 |
| 13 | 0.08 | 5 | 5 | 5 |
| 14 | 0.08 | 5 | 5 | 5 |
| 15 | 0.31 | 5 | 5 | 5 |
| 16 | 1.25 | 5 | 5 | 5 |
| 17 | 1.25 | 5 | 5 | 5 |
| 18 | 1.25 | 5 | 5 | 5 |
| 19 | 1.25 | 4 | 5 | 4 |
| 20 | 1.25 | 5 | 5 | 5 |
| 21 | 0.31 | 5 | 5 | 5 |
| 22 | 1.25 | 5 | 5 | 5 |
| 23 | 1.25 | 5 | 5 | 4 |
| 24 | 1.25 | 5 | 5 | 5 |
| 25 | 0.08 | 5 | 5 | 5 |
| 26 | 0.31 | 5 | 5 | 5 |
| 27 | 1.25 | 5 | 5 | 5 |
| 28 | 1.25 | 5 | 5 | 5 |
| 29 | 0.08 | 5 | 5 | 5 |
| 30 | 1.25 | 5 | 5 | 5 |
| 31 | 1.25 | 4 | 5 | 5 |

TEST EXAMPLE 2

Cylindrical plastic pots (diameter, 10 cm; height, 10 cm) were filled with upland field soil, and the seeds of Japanese millet, radish, tall morningglory and velvetleaf were sowed therein, and cultivated in a greenhouse for 7 days. A designated amount of the test compound formulated in an emulsifiable concentrate as described in F/rmulation Example 2 was diluted with water containing a spreading agent, and the dilution was sprayed over the foliage of the test plants by means of a small sprayer at a spray volume of 10 liters per acre. The test plants were further grown in the greenhouse for 19 days, and the herbicidal activity was examined. The results are shown in Table 4.

TABLE 4

| | | Herbicidal Activity | | | |
|---|---|---|---|---|---|
| Compound No. | Dosage (g/are) | Japanese millet | Radish | Tall morning-glory | Velvet-leaf |
| 1 | 1.25 | 4 | 5 | 5 | 5 |
| 2 | 1.25 | 4 | 5 | 5 | 5 |
| 3 | 1.25 | 5 | 5 | 5 | 5 |
| 4 | 0.31 | 5 | 5 | 5 | 5 |
| 5 | 1.25 | 5 | 5 | 5 | 5 |
| 6 | 0.31 | 5 | 5 | 5 | 5 |
| 7 | 0.31 | 5 | 5 | 5 | 5 |
| 8 | 0.31 | 5 | 5 | 5 | 5 |
| 9 | 0.31 | 5 | 5 | 5 | 5 |
| 10 | 0.31 | 5 | 5 | 5 | 5 |
| 11 | 1.25 | 5 | 5 | 5 | 5 |
| 12 | 0.31 | 5 | 5 | 5 | 5 |
| 13 | 0.31 | 5 | 5 | 5 | 5 |
| 14 | 1.25 | 5 | 5 | 5 | 5 |
| 15 | 0.31 | 5 | 5 | 5 | 5 |
| 16 | 1.25 | 5 | 5 | 5 | 5 |
| 17 | 1.25 | 5 | 5 | 5 | 5 |
| 18 | 1.25 | 5 | 5 | 5 | 5 |
| 19 | 1.25 | 5 | 5 | 5 | 5 |

TABLE 4-continued

| Compound No. | Dosage (g/are) | Herbicidal Activity | | | |
|---|---|---|---|---|---|
| | | Japanese millet | Radish | Tall morning-glory | Velvet-leaf |
| 20 | 0.31 | 5 | 5 | 5 | 5 |
| 21 | 1.25 | 5 | 5 | — | 5 |
| 22 | 1.25 | 5 | 5 | 5 | 5 |
| 23 | 5.0 | 4 | 5 | 5 | 5 |
| 24 | 1.25 | 5 | 5 | 5 | 5 |
| 25 | 0.31 | 5 | 5 | 5 | 5 |
| 26 | 0.31 | 5 | 5 | 5 | 5 |
| 27 | 1.25 | 5 | 5 | 5 | 5 |
| 28 | 0.31 | 5 | 5 | 5 | 5 |
| 29 | 0.31 | 5 | 5 | 5 | 5 |
| 30 | 0.31 | 5 | 5 | 5 | 5 |
| 31 | 1.25 | 5 | 5 | 5 | 5 |

TEST EXAMPLE 3

Cylindrical plastic pots (diameter, 8 cm; height, 12 cm) 7ere filled with paddy field soil, and the seeds of barnyardgrass 7ere sowed in 1 to 2 cm depth. Water 7as poured therein to make a flooded condition, and rice seedlings of 2-leaf stage were transplanted, and the test plants 7ere grown in a greenhouse. After 5 days (at that time the 7eed began to germinate), a designated amount of the test compound formulated in an emulsifiable concentrate as described in F/rmulation Example 2 7as diluted with 2.5 ml of 7ater, and the dilution 7as applied to the water surface. The test plants 7ere grown in the greenhouse for an additional 19 days, and the herbicidal activity and phytotoxicity 7ere examined. The results are shown in Table 5.

TABLE 5

| Compound No. | Dosage (g/are) | Phyto-toxicity Rice plant | Herbicidal activity Barnyard grass |
|---|---|---|---|
| 6 | 0.04 | 0 | 5 |
| 7 | 0.04 | 1 | 5 |
| 8 | 0.04 | 1 | 4 |
| 10 | 0.04 | 1 | 4 |
| 12 | 0.01 | 0 | 4 |
| 13 | 0.01 | 0 | 5 |
| 16 | 0.04 | 0 | 4 |
| 17 | 0.04 | 1 | 4 |
| 18 | 0.04 | 0 | 5 |
| 19 | 0.04 | 0 | 5 |
| 21 | 0.04 | 0 | 4 |
| 31 | 0.04 | 0 | 5 |

TEST EXAMPLE 4

Vats (33 cm×23 cm×11 cm) 7ere filled 7ith upland field soil, and the seeds of corn, black nightshade, giant foxtail and Johnsongrass 7ere sowed in 1 to 2 cm depth. A designated amount of the test compound formulated in an emulsifiable concentrate as described in F/rmulation Example 2 was diluted with 7ater, and the dilution 7as sprayed onto the soil surface by means of a small sprayer at a spray volume of 10 liters per acre. The test plants 7ere grown in a greenhouse for 18 days, and the herbicidal activity and phytotoxicity 7ere examined. The results are shown in Table 6.

TABLE 6

| Compound No. | Dosage (g/are) | Phyto-toxicity Corn | Herbicidal activity | | |
|---|---|---|---|---|---|
| | | | Black nightshade | Giant foxtail | Johnson-grass |
| 2 | 1.25 | 0 | 5 | 5 | 5 |
| 3 | 1.25 | 0 | 5 | 5 | — |
| 4 | 0.08 | 0 | 5 | 4 | 5 |
| 6 | 1.25 | 0 | 5 | 5 | 5 |
| 10 | 0.08 | 1 | 5 | 5 | 5 |
| 13 | 0.04 | 1 | 4 | 4 | 4 |
| 14 | 0.08 | 1 | 5 | 4 | — |
| 16 | 1.25 | 0 | 5 | 5 | 5 |
| 17 | 1.25 | 0 | 5 | 5 | 5 |
| 18 | 1.25 | 0 | 5 | 5 | 5 |
| 19 | 1.25 | 0 | 5 | — | 5 |
| 22 | 0.63 | 0 | 5 | 5 | — |
| 24 | 0.63 | 0 | 5 | 5 | — |
| 26 | 0.08 | 0 | 5 | — | 4 |
| 30 | 0.63 | 1 | 5 | 4 | — |
| 31 | 1.25 | 1 | 5 | — | — |
| A | 1.25 | 0 | 0 | 3 | 0 |
| | 0.08 | 0 | 0 | 0 | 0 |

TEST EXAMPLE 5

Vats (33 cm×23 cm×11 cm) 7ere filled with upland field soil, and the seeds of corn, tall morningglory, velvetleaf and black nightshade 7ere sowed in 1 to 2 cm depth. A designated amount of the test compound formulated in an emulsifiable concentrate as described in Formulation Example 2 7as diluted 7ith 7ater, and the dilution 7as sprayed onto the soil surface by means of a small sprayer at a spray volume of 10 liters per acre. The test plants were grown in a greenhouse for 18 days, and the herbicidal activity and phytotoxicity 7ere examined. The results are shown in Table 7.

TABLE 7

| Compound No. | Dosage (g/are) | Phytotoxicity Corn | Herbicidal activity | | |
|---|---|---|---|---|---|
| | | | Tall morning-glory | Velvet-leaf | Black night-shade |
| 2 | 1.25 | 0 | 5 | 5 | 5 |
| | 0.31 | 0 | 5 | 5 | 5 |
| 16 | 1.25 | 0 | 5 | 5 | 5 |
| | 0.31 | 0 | 5 | 5 | 5 |
| 17 | 1.25 | 0 | 5 | 5 | 5 |
| | 0.31 | 0 | 5 | 5 | 5 |
| 18 | 1.25 | 1 | 5 | 5 | 5 |
| | 0.31 | 0 | 5 | 4 | 5 |
| 19 | 1.25 | 0 | 5 | 5 | 5 |
| 30 | 0.63 | 1 | 5 | 5 | 5 |
| 31 | 1.25 | 1 | 4 | 4 | 5 |
| A | 1.25 | 0 | 0 | 1 | 0 |
| | 0.31 | 0 | 0 | 0 | 0 |

TEST EXAMPLE 6

Vats (33 cm×23 cm×11 cm) 7ere filled 7ith upland field soil, and the seeds of cotton, tall morningglory, black nightshade and giant foxtail 7ere sowed in 1 to 2 cm depth. A designated amount of the test compound formulated in an emulsifiable concentrate as described in F/rmulation Example 2 7as diluted 7ith water, and the dilution 7as sprayed onto the soil surface by means of a small sprayer at a spray volume of 10 liters per acre. The test plants 7ere grown in a greenhouse for 18 days, and the herbicidal activity and phytotoxicity 7ere examined. The results are shown in Table 8.

TABLE 8

| Compound No. | Dosage (g/are) | Phytotoxicity Cotton | Herbicidal activity Tall morning-glory | Black night-shade | Giant foxtail |
|---|---|---|---|---|---|
| 3 | 0.31 | 1 | 5 | 5 | 5 |
| 4 | 0.31 | 1 | 5 | 5 | 5 |
| 6 | 1.25 | 0 | 5 | 5 | 5 |
| 10 | 0.31 | 1 | 5 | 5 | 5 |
|  | 0.08 | 0 | 5 | 5 | 5 |
| 13 | 0.16 | 0 | 5 | 5 | 5 |
| 15 | 0.63 | 0 | 5 | 5 | 5 |
|  | 0.16 | 0 | 4 | 5 | 4 |
| 22 | 0.63 | 0 | 5 | 5 | 5 |
| 24 | 0.63 | 0 | 5 | 5 | 5 |
|  | 0.31 | 0 | 5 | 5 | 4 |
| 25 | 0.16 | 1 | 5 | 5 | 5 |
| 27 | 1.25 | 0 | 5 | 5 | 5 |
|  | 0.31 | 0 | 5 | 5 | 4 |
| 28 | 0.31 | 1 | 5 | 5 | 4 |
| 29 | 0.31 | 1 | 5 | 5 | 5 |
|  | 0.16 | 1 | 5 | 5 | 5 |
| A | 1.25 | 2 | 0 | 0 | 3 |
|  | 0.31 | 0 | 0 | 0 | 2 |

TEST EXAMPLE 7

Vats (33 cm×23 cm×11 cm) were filled with upland field soil, and the seeds of corn, tall morningglory, velvetleaf, black nightshade and common cocklebur were sowed therein, and cultivated in a greenhouse for 16 days. A designated amount of the test compound formulated in an emulsifiable concentrate as described in F/rmulation Example 2 7as diluted 7ith 7ater, and the dilution 7as sprayed over the foliage of the test plants by means of a small sprayer at a spray volume of 10 liters per acre. At the time of the application, the test plants were generally at the 0.5 to 4 leaf stage and in 5 to 30 cm height, although the growing stage of the test plants varied depending on their weed species. The test plants 7ere further grown in the greenhouse for 18 days, and the herbicidal activity and phytotoxicity were examined. The results are shown in Table 9.

TABLE 9

| Compound No. | Dosage (g/are) | Phyto-toxicity Corn | Herbicidal activity Tall morning-glory | Velvet-leaf | Black night-shade | Common cockle-bur |
|---|---|---|---|---|---|---|
| 1 | 0.31 | 1 | 5 | 5 | 5 | 5 |
| 2 | 0.16 | 0 | 5 | 5 | 5 | 5 |
| 3 | 0.31 | 1 | 5 | 5 | 5 | 5 |
| 4 | 0.16 | 1 | 5 | 5 | 5 | 5 |
|  | 0.04 | 1 | 5 | 5 | 5 | 5 |
| 5 | 0.16 | 1 | 5 | 5 | 5 | 4 |
| 6 | 0.04 | 1 | 5 | 5 | 5 | — |
| 7 | 0.04 | 1 | 5 | 5 | 5 | 4 |
| 8 | 0.16 | 1 | 5 | 5 | 5 | 4 |
| 9 | 0.04 | 1 | 5 | 5 | 5 | 4 |
| 10 | 0.04 | 1 | 5 | 5 | 5 | 5 |
| 12 | 0.01 | 0 | 5 | 5 | 5 | 4 |
| 14 | 0.04 | 1 | 5 | 5 | 5 | 5 |
| 15 | 0.04 | 1 | 5 | 5 | 5 | 4 |
| 16 | 0.16 | 1 | 5 | 5 | 5 | 4 |
|  | 0.04 | 1 | 5 | 5 | 5 | 4 |
| 17 | 0.16 | 1 | 5 | 5 | 5 | 5 |
|  | 0.04 | 1 | 5 | 5 | 5 | 4 |
| 18 | 0.16 | 1 | 5 | 5 | 5 | 5 |
| 19 | 0.04 | 1 | 5 | 5 | 5 | — |
| 23 | 0.16 | 0 | 5 | 5 | 5 | 4 |
| 25 | 0.04 | 1 | 5 | 5 | 5 | 4 |

TEST EXAMPLE 8

Vats (33 cm×23 cm×11 cm) 7ere filled 7ith upland field soil, and the seeds of wheat, barley, Persian speedwell, wild buckwheat and catchweed bedstraw were sowed in 1 to 2 cm depth. A designated amount of the test compound formulated in an emulsifiable concentrate as described in F/rmulation Example 2 was diluted with 7ater, and the dilution 7as sprayed onto the soil surface by means of a small sprayer at a spray volume of 10 liters per are. The test plants 7ere grown in a greenhouse for 25 days, and the herbicidal activity and phytotoxicity 7ere examined. The results are shown in Table 10.

TABLE 10

| Compound No. | Dosage (g/are) | Phytotoxicity Wheat | Phytotoxicity Barley | Herbicidal activity Persian speed-well | Wild buck-wheat | Catch-weed bedstraw |
|---|---|---|---|---|---|---|
| 2 | 1.25 | 0 | 0 | 5 | 5 | 5 |
| 16 | 1.25 | 0 | 0 | 5 | 5 | 5 |
| 17 | 1.25 | 0 | 0 | 5 | 5 | 5 |
| 18 | 1.25 | 0 | 0 | 5 | 5 | 5 |
| 30 | 0.16 | 0 | 0 | 5 | 5 | 5 |

TEST EXAMPLE 9

Vats (33 cm×23 cm×11 cm) 7ere filled with upland field soil, and the seeds of 7heat, Persian speedwell, 7ild buckwheat and catchweed bedstraw 7ere sowed therein, and cultivated in a greenhouse for 29 days. A designated amount of the test compound formulated in an emulsifiable concentrate as described in F/rmulation Example 2 7as diluted with 7ater, and the dilution 7as sprayed over the foliage of the test plants by means of a small sprayer at a spray volume of 10 liters per are. At the time of the application, the test plants 7ere generally at the 1 to 4 leaf stage and in 3 to 25 cm height, although the growing stage of the test plants varied depending on their 7eed spieces. The test plants were further grown in the greenhouse for 25 days, and the herbicidal activity and phytotoxicity were examined. The results are shown in Table 11.

TABLE 11

| Compound No. | Dosage (g/are) | Phytotoxicity Wheat | Herbicidal activity Persian speed-well | Wild buck-wheat | Catch-weed bedstraw |
|---|---|---|---|---|---|
| 2 | 0.63 | 0 | 5 | 5 | 5 |
|  | 0.16 | 0 | 5 | 5 | 4 |
| 4 | 0.16 | 1 | 5 | 5 | 5 |
|  | 0.04 | 0 | 5 | 5 | 4 |
| 5 | 0.63 | 1 | 5 | — | 5 |
| 6 | 0.16 | 0 | 5 | — | 5 |
| 7 | 0.16 | 0 | 5 | — | 5 |
| 8 | 0.16 | 0 | 5 | 5 | 5 |
| 9 | 0.04 | 1 | 5 | 5 | 4 |
| 10 | 0.04 | 1 | 5 | 5 | 4 |
| 12 | 0.16 | 1 | 5 | 5 | 5 |
| 13 | 0.04 | 1 | 5 | 5 | 4 |
| 16 | 0.16 | 1 | 5 | 5 | 5 |
| 19 | 0.16 | 0 | 5 | 5 | 4 |
| 22 | 0.63 | 0 | 5 | 5 | 5 |
| 23 | 0.63 | 0 | 5 | 5 | 4 |
| 24 | 0.16 | 0 | 5 | 5 | 4 |
| 25 | 0.16 | 1 | 5 | 5 | 5 |
| 29 | 0.16 | 0 | 4 | 5 | 5 |

What is claimed is:

1. A compound of the formula:

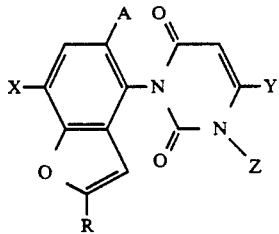

(I)

Therein A is hydrogen, fluorine or chlorine; X is hydrogen, fluorine, chlorine or bromine; Y is methyl optionally substituted with halogen; Z is methyl or amino; R is halo($C_1$-$C_5$)alkyl, ($C_1$-$C_5$)alkylthio($C_1$-$C_5$)alkyl, amino($C_1$-$C_5$)alkyl, ($C_1$-$C_5$)alkylamino($C_1$-$C_5$)alkyl, ($C_1$-$C_5$)acylamino($C_1$-$C_5$)alkyl, ($C_1$-$C_5$)alkylsulfonylamino($C_1$-$C_5$)alkyl, $C_1$-$C_5$ acyl, hydroxy($C_1$-$C_5$)alkyl, ($C_1$-$C_5$)alkoxy($C_1$-$C_5$)alkyl, ($C_1$-$C_5$)alkoxy($C_1$-$C_5$)alkoxy($C_1$-$C_5$)alkyl, ($C_1$-$C_5$)acyloxy($C_1$-$C_5$)alkyl, hydroxyimino($C_1$-$C_5$)alkyl, ($C_1$-$C_5$)alkoxyimino($C_1$-$C_5$)alkyl, cyano, hydrazono($C_1$-$C_5$)alkyl, ($C_1$-$C_5$)alkylhydrazono($C_1$-$C_5$)alkyl, phenylhydrazono($C_1$-$C_5$)alkyl (Therein the phenyl is optionally substituted with $C_1$-$C_5$ alkyl, $C_1$-$C_5$ alkoxy, halo($C_1$-$C_5$)alkyl, halo($C_1$-$C_5$)alkoxy, halogen, nitro, cyano or $C_1$-$C_5$ alkylthio), carboxy, $C_1$-$C_5$ alkoxycarbonyl, aminocarbonyl, $C_1$-$C_5$ alkylaminocarbonyl or phenylaminocarbonyl (Therein the phenyl is optionally substituted with $C_1$-$C_5$ alkyl, $C_1$-$C_5$ alkoxy, halo($C_1$-$C_5$)alkyl, halo($C_1$-$C_5$)alkoxy, halogen, nitro, cyano or $C_1$-$C_5$ alkylthio).

2. A compound according to claim 1, Therein A is fluorine or chlorine, X is fluorine or chlorine, Y is trifluoromethyl or chlorodifluoromethyl, Z is methyl and R is halo($C_1$-$C_5$)alkyl, $C_1$-$C_5$ acyl, hydroxy($C_1$-$C_5$)alkyl, ($C_1$-$C_5$)alkoxy($C_1$-$C_5$)alkyl, ($C_1$-$C_5$)alkoxy($C_1$-$C_5$)alkoxy($C_1$-$C_5$)alkyl, ($C_1$-$C_5$)acyloxy($C_1$-$C_5$)alkyl, hydroxyimino($C_1$-$C_5$)alkyl, ($C_1$-$C_5$)alkoxyimino($C_1$-$C_5$)alkyl, cyano, ($C_1$-$C_5$)alkylhydrazono($C_1$-$C_5$)alkyl, carboxy, $C_1$-$C_5$ alkoxycarbonyl or amino carbonyl.

3. A compound according to claim 2, Therein A is fluorine and Y is trifluoromethyl.

4. A compound according to claim 2, wherein R is hydroxy($C_1$-$C_5$)alkyl, ($C_1$-$C_5$)alkoxy($C_1$-$C_5$)alkyl, ($C_1$-$C_5$)acyloxy($C_1$-$C_5$)alkyl, carboxy or $C_1$-$C_5$ alkoxycarbonyl.

5. A compound according to claim 1, wherein A is fluorine, X is fluorine or chlorine, Y is trifluoromethyl, Z is methyl and R is hydroxy($C_1$-$C_5$)alkyl, ($C_1$-$C_5$)alkoxy($C_1$-$C_5$)alkyl, ($C_1$-$C_5$)acyloxy($C_1$-$C_5$)alkyl, carboxy or $C_1$-$C_5$ alkoxycarbonyl.

6. A compound according to claim 1, Thich is 1-(2-carboxy-7-chloro-5-fluorobenzo[b]furan-4-yl)-3-methyl-4-trifluoromethyl-1,2,3,6-tetrahydropyrimidin-2,6-dione.

7. A compound according to claim 1, Thich is 1-(7-chloro-5-fluoro-2-methoxycarbonylbenzo[b]furan-4-yl)-3-methyl-4-trifluoromethyl-1,2,3,6-tetrahydropyrimidin-2,6-dione.

8. A compound according to claim 1, which is 1-(5,7-difluoro-2-hydroxymethylbenzo[b]furan-4-yl)-3-methyl-4-trifluoromethyl-1,2,3,6-tetrahydropyrimidin-2,6-dione.

9. A compound according to claim 1, Thich is 1-(2-acetoxymethyl-5,7-difluorobenzo[b]furan-4-yl)-3-methyl-4-trifluoromethyl-1,2,3,6-tetrahydropyrimidin-2,6-dione.

10. A compound according to claim 1, Therein A is fluorine or chlorine, X is fluorine or chlorine, Y is trifluoromethyl or chlorodifluoromethyl, Z is methyl and R is selected from the group consisting of —CHO, —COOH, —CH$_2$OH, —CH(CH$_3$)OH, —CH=NOH, —CH=NOCH$_3$, —CH=NOC$_2$H$_5$, —CN, —CH$_2$OCH$_2$OCH$_3$, —CH$_2$OCH$_3$, —CH$_2$OC(O)CH$_3$, —COCH$_3$, —CH(CH$_3$)OCH$_3$, —CH(CH$_3$)OC(O)CH$_3$, —C(CH$_3$)=OH, —COOCH$_3$, —COOC$_2$H$_5$, —COOCH(CH$_3$)$_2$, —COOC$_5$H$_{11}$(n), —CONH$_2$, —CH=N—(CH$_3$)$_2$, —CH$_2$Br, —CHBr$_2$, —CBr$_3$ and CH$_2$OC(O)CF$_3$.

11. A herbicidal composition comprising as an active ingredient a herbicidally effective amount of the compound according to claim 1, and an inert carrier or diluent.

12. The herbicidal composition according to claim 11, Therein the compound of formula (I) is present in an amount of from 0.001% to 80% by weight based on the total weight of the composition.

13. The herbicidal composition according to claim 11, Therein the compound of formula (I) is present in an amount of from 0.003% to 70% by weight based on the total weight of the composition.

14. A method for exterminating undesired weeds, Thich comprises applying a herbicidally effective amount of the compound according to claim 1 to an area There the undesired weeds grow or will grow.

* * * * *

UNITED STATES PATENT AND TRADEMARK OFFICE
CERTIFICATE OF CORRECTION

PATENT NO. : 5,308,829
DATED : May 3, 1994
INVENTOR(S) : Susumu TAKEMURA, Masayuki ENOMOTO, Toru UEKAWA, Masaharu SAKAKI, Ryo SATO and Eiki NAGANO It is certified that error appears in the above-indentified patent and that said Letters Patent is hereby corrected as shown below:

On title page, item
"[21] Appl. No." Section indicating the Serial Number of the application such that the incorrect number of "38,564" is corrected so as to read --33,564--.

Signed and Sealed this

Twenty-seventh Day of September, 1994

Attest:

BRUCE LEHMAN

Attesting Officer

Commissioner of Patents and Trademarks